United States Patent [19]

Roger et al.

[11] Patent Number: 4,871,843

[45] Date of Patent: Oct. 3, 1989

[54] CYCLIC BENZENESULFONAMIDES, PROCESS FOR THEIR PREPARATION AND THEIR USE AS ACTIVE SUBSTANCE OF PHARMACEUTICAL COMPOSITIONS

[75] Inventors: Pierre Roger, Montigny-les-Bretonneux; Patrick Choay, Paris; Jean-Paul Fournier, Versailles, all of France

[73] Assignee: DROPIC–Societe Civile de gestion de droits de Propriete Industrielle, Paris, France

[21] Appl. No.: 224,549

[22] Filed: Jul. 26, 1985

Related U.S. Application Data

[62] Division of Ser. No. 662,178, Oct. 18, 1984, Pat. No. 4,760,062.

[30] Foreign Application Priority Data

Oct. 18, 1983 [FR] France ................... 83 1655

[51] Int. Cl.[4] ............... C07D 243/08; C07D 295/22
[52] U.S. Cl. ........................ 540/575; 540/544; 540/604; 544/159; 544/383; 546/236
[58] Field of Search ............... 544/383; 540/575

[56] References Cited

U.S. PATENT DOCUMENTS

| | | | |
|---|---|---|---|
| 2,415,786 | 2/1947 | Buck ................... | 544/383 |
| 2,507,408 | 5/1950 | Jacob ................... | 544/383 |
| 3,464,971 | 9/1969 | Weaver et al. .......... | 544/383 |
| 3,829,487 | 8/1974 | Mrozik ................. | 544/383 |
| 4,159,331 | 6/1979 | McCall ................. | 544/363 |

FOREIGN PATENT DOCUMENTS

| | | |
|---|---|---|
| 874443 | 3/1953 | Fed. Rep. of Germany . |
| 2335950 | 1/1975 | Fed. Rep. of Germany . |
| 816988 | 8/1937 | France . |
| 2301255 | 9/1976 | France . |
| 302372 | 10/1954 | Switzerland . |

OTHER PUBLICATIONS

Horstmaan et al., *Arzneimittel-Forschung*, vol. 17, No. 6, pp. 653-659 (1967).
Keasling et al., *Journal of Medicinal Chemistry*, vol. 8, No. 4, pp. 547-549 (1965).
Oridzheva et al., *Chemical Abstracts*, vol. 77, pp. 411, 113957A (1972).

*Primary Examiner*—Glennon H. Hollrah
*Assistant Examiner*—James H. Turnipseed
*Attorney, Agent, or Firm*—Foley & Lardner, Schwartz, Jeffery, Schwaab, Mack, Blumenthal & Evans

[57] ABSTRACT

The invention relates to new N-cyclic benzenesulfonamides, their process of preparation and their use as active substance of pharmaceutical compositions. The new benzenesulfonamides according to the invention correspond to the following general formula (I):

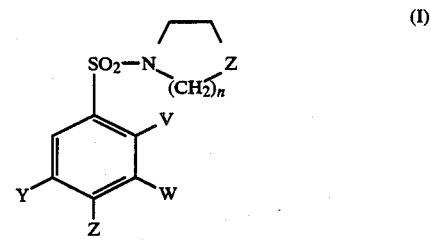

in which:
V represents, for example, hydrogen,
W represents, for example $CF_3$,
X represents, for example, hydrogen,
Y represents, for example, hydrogen,
n is 2 or 3,
Z represents, for example, the group $NR_4$, in which $R_4$ represents, for example, hydrogen.

These compounds are useful in pharmaceutical compositions for the treatment of nervous disorders with anxiety.

6 Claims, No Drawings

CYCLIC BENZENESULFONAMIDES, PROCESS FOR THEIR PREPARATION AND THEIR USE AS ACTIVE SUBSTANCE OF PHARMACEUTICAL COMPOSITIONS

This application is a division of copending application Ser. No. 662,178, filed Oct. 18, 1984, now U.S. Pat. No. 4,760,062.

The invention relates to new medicaments which have activity on the central nervous system, particularly the anxiolytic activity, and which contain, as active principle, compounds having a basic structure of the benzenesulfonamide type as well as their salts obtained with physiologically acceptable acids.

The term "medicament" hereafter means any pharmaceutical composition containing in association with a pharmaceutically acceptable vehicle, one at least of the chemical compounds such as defined below.

The invention also relates to a process of preparing the above-said chemical compounds as well as their salts.

Some benzenesulfonamides or their preparation have already been described in the documents mentioned below.

The compounds of the following formula:

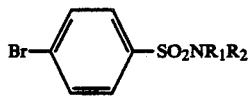

in which $NR_1R_2$ represents the piperidino, morpholino, or methylpiperazino group, are presented in J. Med. Chem., vol. 8, 1965, with a family of compounds possessing an anticonvulsant activity. However, according to the results relating to anticonvulsant activity and shown in table I of the abovesaid article, the three particular compounds whose respective formulae have just been mentioned above do not show the anticonvulsant activity of the family of compounds to which they belong.

The compound of formula:

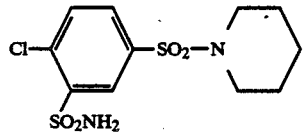

is mentioned in the article Arzneimittelforschung, Heft 6, June 1967, page 654, as antidiuretic.

The compounds of the following formulae:

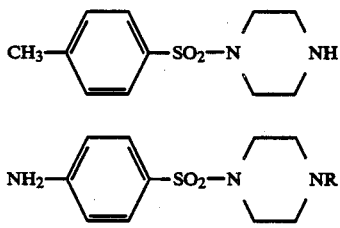

R representing the $CH_3$, $C_2H_5$,

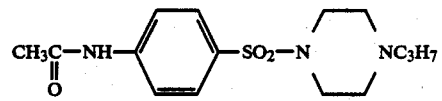

are known from the patent U.S. No. 2 415 786, but no indication of their properties is mentioned.

The patent U.S. No. 2 507 408 relates to compounds of the following formula:

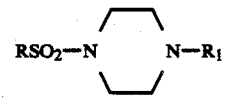

in which R represents a group selected from among alkyl radicals containing from 1 to 4 carbon atoms, phenyl radicals which may be substituted by a member of the class constituted by lower alkyls, amino, methoxy, ethoxy, halogen and $R_1$ represents an alkyl radical containing no more than 3 carbon atoms.

It is mentioned that the use of these compounds may be contemplated for the treatment of traumatic and haemorragic shock, without any other indication.

The compound presented as preferred one does not possess a benzene group since it is ethanesulfonyl-1-ethyl-4-piperazine.

The U.S. Pat. No. 3 829 487 relates to compounds of formula:

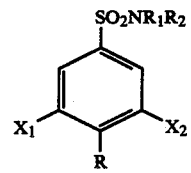

in which R represents a hydrogen atom or an amino group, $X_1$ and $X_2$ each represent a halogen atom, a trifluoromethyl or nitro group, $R_1$ and $R_2$ represent a hydrogen atom, a lower alkoxy radical, or a substituted lower alkyl radical in which the substituents are lower alkoxy, lower alkylthio, lower alkylsulfinyl, lower alkylsulfonyl, cyano, halogen groups, or $R_1$ and $R_2$ may form with the nitrogen atom a heterocyclic ring of 3 to 6 members, for example saturated heterocyclic rings containing a nitrogen atom, such as aziridinyl, azetidinyl, pyrrolidinyl, piperidinyl.

The group of compounds is presented as being antiparasitic and antihelmintic agents, advantageously used at very high doses in the treatment of bovine and ovine liver fluke.

In the preferred compounds, $R_1$ and $R_2$ represent lower alkyl radicals, but do not form, in combination with N, a heterocyclic nitrogen ring.

The compounds of formula:

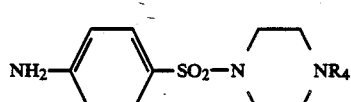

in which $R_4$ represents a substituted or unsubstituted phenyl group, are used according to U.S. Pat. No. 4 159 331 as intermediate products in the synthesis of the compounds 4-(quinolinylaminophenyl) sulfonyl piperazine substituted at the 1-position.

The compounds of the formula:

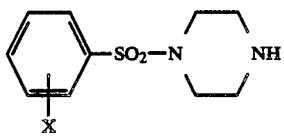

in which X represents Cl, CH₃, NO₂, NH₂ are presented as having analgesic activity as well as pharmacological activity in the cardiovascular system, without any other precision.

The preparation of the compound of the formula:

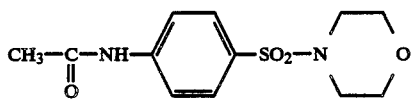

is described in the Swiss Pat. No. 302 372, but nothing is mentioned on the properties of this compound.

Chemical Abstracts, vol. 77, 1972, page 411, 113 957a mention the compounds of formula: 2,5-(CH₃O)₂C₆H₅SO₂R in which R may represent a morpholino or piperidino group.

However nothing is mentioned on the properties of these compounds.

The preparation of the compound of the formula:

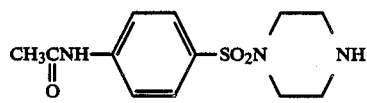

os described in German Pat. No. 874 443; this compound is presented as having a bactericidal activity, without any other precision.

The compound of the formula:

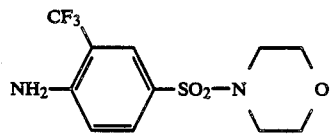

is presented in DOS No. 23 35950 as an intermediate of synthesis of dyes.

The synthesis of the compound 4-aminobenzene-sulfonyl piperidine is indicated in French Pat. No. 816 988; this compound is presented as belonging to a family of compounds having an anti-streptococcal and anti-staphylococcal activity, without any other precision.

The medicaments according to the invention are characterized in that they contain as active substance, one at least of the compounds corresponding to the following general formula (I):

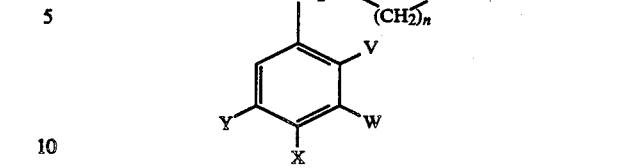

in which:

V represents hydrogen, an $OR_1$ radical in which $R_1$ represents an alkyl group of 1 to 4 carbon atoms;

W represents hydrogen, the group $CF_3$;

X represents hydrogen, halogen, a $NO_2$ group, a $NH_2$ group, a $NH-CO-R_2$ radical in which $R_2$ represents an alkyl radical of 1 to 4 carbon atoms or aryl, an $OR_1$ radical in which $R_1$ represents an alkyl radical of 1 to 4 carbon atoms;

Y represents hydrogen, halogen, a $NO_2$ group, a $NH_2$ group, $CF_3$, a $NH-CO-R_2$ radical in which $R_2$ represents an alkyl radical of 1 to 4 carbon atoms or aryl, an $OR_1$ radical in which $R_1$ represents an alkyl radical of 1 to 4 carbon atoms, an $SO_2-R_3$ radical in which $R_3$ represents an alkyl radical of 1 to 4 carbon atoms, n is 2 or 3;

Z represents an oxygen atom, the group $CH_2$ or $NR_4$ in which:

$R_4$ represents:

a hydrogen a lower alkyl radical of 1 to 6 carbon atoms, hydroxyalkyl radical of 1 to 3 carbon atoms, a cycloalkanoyl radical of 3 to 10 carbon atoms, an aryl radical unsubstituted or substituted by halogen, by the group $CF_3$, by a radical $OR_1$ in which $R_1$ represents an alkyl radical having 1 to 4 carbon atoms, an aralkyl radical in which the aliphatic chain has 1 to 4 carbon atoms and may include C═O and C—OH groups in which the aryl group is unsubstituted or substituted by halogen, by group $CF_3$, by a radical $OR_1$, in which $R_1$ is an alkyl radical having 1 to 4 carbon atoms, an aryl radical or its isosters unsubstituted or substituted by a halogen, by a $CF_3$ group, by a radical $OR_1$ in which $R_1$ is an alkyl group of 1 to 4 carbon atoms; and provided when n is 2, that:

either V represents a radical $OR_1$ and one at least of the elements X, Y and W is different from hydrogen; or:

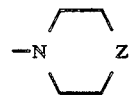

represents a

group, $R_4$ having the above-mentioned meaning, and Y or W represent $CF_3$.

In other words, the compounds which constitute the active substance of this group of medicaments according to the invention have a structure which, when n is 2, comprises:

either a piperazino group and a benzenic ring substituted at the meta position by a CF<sub>3</sub> group;

or a piperazino, morpholino or piperidino group and a benzenic ring at least disubstituted, one of the two substituents being an alkoxy group at the ortho position.

This group of medicaments will be denoted by G1 in the following.

The invention also relates to the addition salts of the compounds of formula (I) obtained with physiologically acceptable organic or inorganic acids.

As physiologically acceptable organic or inorganic salts, may be mentioned, for example, the hydrochloride, the hydrobromide, the sulfates, the phosphates, the methane sulfonate, the acetate, the fumarate, the succinate, the lactate, the pyruvate, the citrate, the tartrate, the maleate, the malonate, the benzoate, the salicylate, the 2,6-dichlorobenzoate, the trimethoxy benzoate, the diaminobenzen sulfonate, the chromoglycate, the benzene sulfonate, the dipropyl acetate, the 1-glucose phosphate.

Another preferred group of medicaments according to the invention is constituted by those whose active substance is a compound of formula (I):

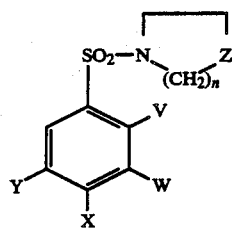

(I)

in which V, W, X, Y, Z and n have the above-indicated meanings and provided that when n is 2:

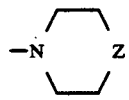

represents a

group, R<sub>4</sub> having the above-indicated meaning, and: either W or Y represent a CF<sub>3</sub> group, or V represents a OR<sub>1</sub> radical and one at least of the elements X, Y and W is different from hydrogen.

In other words, the compounds which constitute the active substance of this group of medicaments according to the invention have a structure which, when n is 2, comprises:

either a piperazino group and an aromatic ring at least disubstituted, one of the substituants being an alcoxy radical at the ortho position;

or a piperazino group and an aromatic ring substituted at the meta position by CF<sub>3</sub>.

This group of compounds will be denoted by G1bis in the following.

A preferred group of medicaments according to the invention is constituted by those whose active substance is a compound of formula (I), in which Z represents O and corresponds to following formula (II):

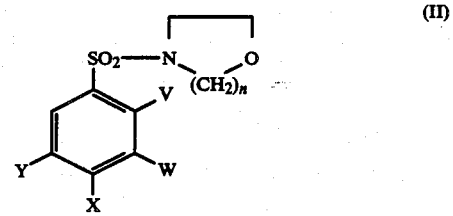

(II)

in which X, Y, V and W have the above-indicated meanings.

This group will be denoted by G2 in the following.

A preferred group of medicaments according to the invention is constituted by those whose active substance is a compound of formula (I), in which Z represents CH<sub>2</sub> and corresponds to the following formula (III):

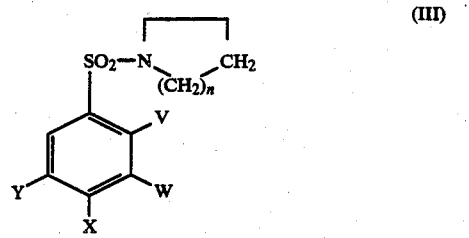

(III)

in which X, Y, V and W have the above-indicated meaning.

This group will be denoted by G3 in the following.

A preferred group of medicaments according to the invention is constituted by those whose active substance is a compound of formula (I), in which Z represents NR<sub>4</sub> and corresponds to the following formula (IV):

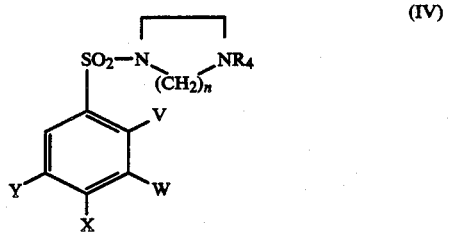

(IV)

in which X, Y, V, W, R<sub>4</sub> and n have the above-indicated meanings.

This group will be denoted in the following by G4.

Among the group G4, a preferred class of medicaments is constituted by those of which the active substance is a compound in which R<sub>4</sub> represents a cyclopropanoyl, cyclopentanoyl, cyclohexanoyl, adamantoyl radical, a benzoyl radical or furoyl.

This group will be denoted by G5 in the following.

Another preferred group of medicaments according to the invention is constituted by those of the group G4, of which the active substance is a compound in which R<sub>4</sub> represents H and corresponding to the following formula (VI):

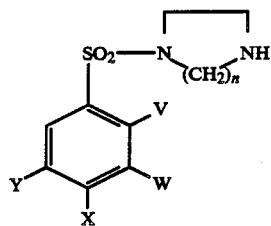

(VI)

in which X, Y, V, W have the above-indicated meanings.

This group will be denoted by G6 in the following.

Another preferred group of medicaments according to the invention is constituted by those of the group G4 of which the active substance is a compound in which Z represents NR₄ where R₄ represents:

a benzyl radical unsubstituted or substituted by halogen, by the group CF₃, by the radical OR₁ in which R₁ is an alkyl of 1 to 4 carbon atoms, groups CH₃, CH₂CH₂OH, CH₂CH₂CH₂OH, CH₂CHOHCH₂OH, CH₂—C₆H₅,

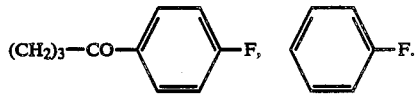

This group will be denoted in the following by G7.

A preferred group of medicaments according to the invention is constituted by those whose active substance is a compound of formula (I), in which n is 2 and corresponding to the following formula (VIII):

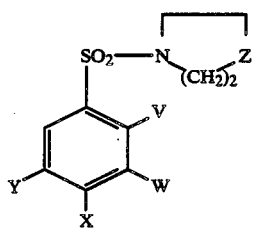

(VIII)

in which X, Y, V and W have the above-indicated meaning.

This group will be denoted by G8 in the following.

Another preferred group of medicaments according to the invention is constituted by those of which the active substance is a compound of formula (I), in which n is 3 and corresponding to the following formula (IX):

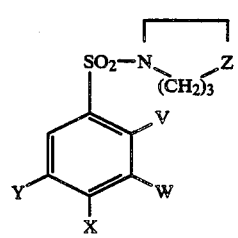

(IX)

in which X, Y, V and W have the above-indicated meanings.

This group will be denoted by G9 in the following.

Another preferred group of medicaments according to the invention is constituted by those of which the active substance is a compound of formula (I), in which V represents OCH₃, W represents H and corresponding to the following formula (X):

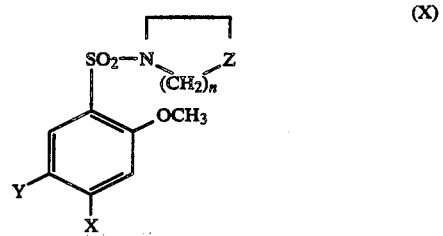

(X)

in which X represents H, NO₂, OCH₃, Y represents H, Cl, Br, OCH₃, SO₂CH₃, SO₂iC₃H₇, CF₃, Z and n have the above-indicated meanings.

This group will be denoted by G10 in the following.

Another preferred group of medicaments according to the invention is constituted by those of which the active substance is a compound of formula (I), in which V represents H, W represents CF₃ and corresponding to the following formula (XI):

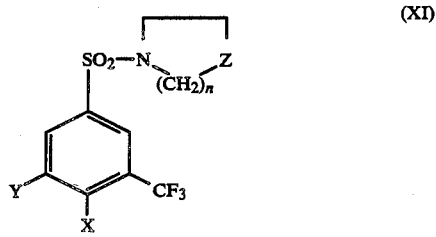

(XI)

in which X represents H, Cl and Y represents H, CF₃, Z and n have the above-indicated meanings.

This group will be denoted by G11 in the following.

Among the group G10, a preferred group of medicaments according to the invention is constituted by those of which the active substance is a compound of formula (I), in which V represents OCH₃, W represents H, X represents OCH₃ and corresponding to the following formula (XII):

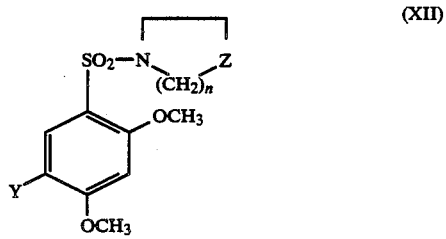

(XII)

in which Y represents H, SO₂iC₃H₇, Br, Cl, SO₂CH₃, OCH₂, Z and n have the above-indicated meanings.

This group will be denoted by G12 in the following.

Among the group G10, another preferred group of medicaments according to the invention is constituted by those of which the active substance is a compound of formula (I), in which V represents OCH₃, W represents H, X represents H and corresponding to the following formula (XIII):

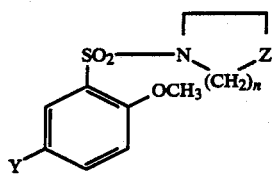

(XIII)

in which Y represents Br or Cl, Z and n have the above-indicated meaning.

This group will be denoted by G13 in the following.

Among the group G10, another preferred group of medicaments according to the invention is constituted by those of which the active substance of the formula (I) in which V represents $OCH_3$, W represents H, X has the meanings indicated in the definition of G10, but is different from hydrogen, Y represents hydrogen and corresponding to following formula (XIIIa):

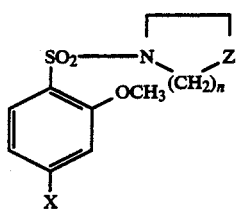

(XIIIa)

in which Z has the above-indicated meaning.

This group will be denoted by G13a in the following.

Among the group G10, another preferred group of medicaments according to the invention is constituted by those of which the active substance is a compound of formula (I), in which V represents $OCH_3$, W represents H, X represents $NO_2$ and corresponding to the following formula (XIV):

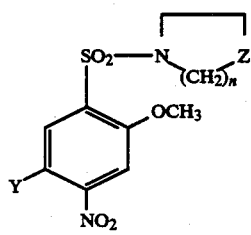

(XIV)

in which Y represents H or Cl, Z and n have the meanings indicated above.

This group will be denoted by G14 in the following.

Among the group G11, another preferred group of medicaments according to the invention is constituted by those of which the active substance is a compound of formula (I), in which V represents H, W represents $CF_3$, X represents H and corresponding to the following formula (XV):

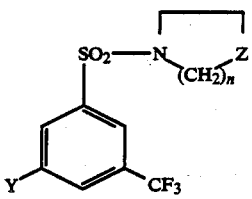

(XV)

in which Y represents H or $CF_3$, Z and n have the above-indicated meanings.

This group will be denoted by G15 in the following.

Among the group G11, a preferred group of medicaments according to the invention is constituted by those of which the active substance is a compound of formula (I) in which V represents H, W represent $CF_3$, X represents Cl, Y represents H and corresponds to the following formula (XVa):

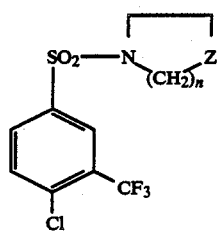

(XVa)

and Z and n have the above-indicated meanings.

Among the group G1, a preferred group of medicaments is constituted by those of formula (I) in which V, X and Y have the meanings indicated in the definition of G1 and W represents $CF_3$, corresponding to the following general formula (XVb):

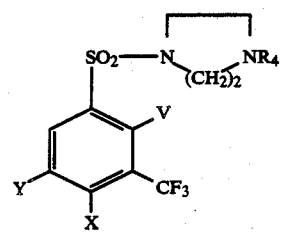

(XVb)

in which $R_4$ has the above-indicated meaning.

This group will be denoted by G15b in the following.

Among the group G1, a preferred group of medicaments according to the invention is constituted by those of formula (I), in which V, X and Y have the meanings indicated in the definition of G1, W represents $CF_3$ and corresponding to formula (XVc):

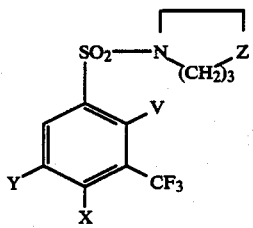

(XVc)

in which Z has the above-indicated meaning.

This group will be denoted by G15c in the following.

A preferred group of medicaments according to the invention is constituted by those of which the active substance is a compound corresponding to the following formula:

| Compound n° | Structure |
|---|---|
| 1 211 | 2,4-dimethoxy-5-methylsulfonyl-phenyl-SO₂-N(CH₂)₂CH₂ (cyclic) |
| 1 224 | 5-chloro-2,4-dimethoxyphenyl-SO₂-N(CH₂)₂CH₂ (cyclic) |
| 1 242 | 2,4-dimethoxy-5-methylsulfonyl-phenyl-SO₂-N(CH₂)₂NH (cyclic) |
| 1 247 | 5-chloro-2-methoxyphenyl-SO₂-N(CH₂)₂O (cyclic) |
| 1 265 | 2,4,5-trimethoxyphenyl-SO₂-N(CH₂)₂N-CH₂CHOHCH₂OH (cyclic) |
| 1 270 | 5-chloro-2,4-dimethoxyphenyl-SO₂-N(CH₂)₂N-CO-adamantyl (cyclic) |
| 1 301 | 2,4,5-trimethoxyphenyl-SO₂-N(CH₂)₃NH (cyclic) |
| 1 304 | 2,4,5-trimethoxyphenyl-SO₂-N(CH₂)₃N-CO-furyl (cyclic) |
| 1 306 | 2,4-dimethoxy-5-methylsulfonyl-phenyl-SO₂-N(CH₂)₃N-CO-furyl (cyclic) |

A preferred group of medicaments according to the invention is constituted by those of which the active substance is a compound corresponding to the following formula:

| Compound n° | Structure |
|---|---|
| 1 334 | 3-trifluoromethylphenyl-SO₂-N(CH₂)₂N-CH₂-CHOH-CH₂OH (cyclic) |
| 1 400 | 3,5-bis(trifluoromethyl)phenyl-SO₂-N(CH₂)₂NH (cyclic) |
| 1 399 | 4-chloro-3-trifluoromethylphenyl-SO₂-N(CH₂)₃NH (cyclic) |

| Compound n° | |
|---|---|
| 1 389 | 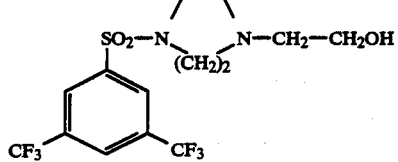 |
| 1 397 | 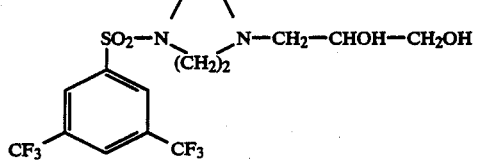 |
| 1 390 | 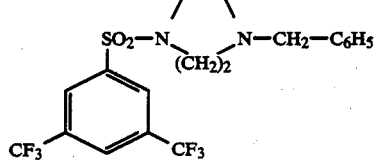 |
| 1 336 | 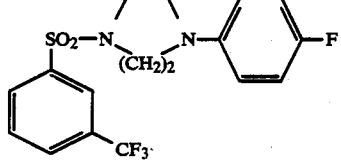 |
| 1 392 | 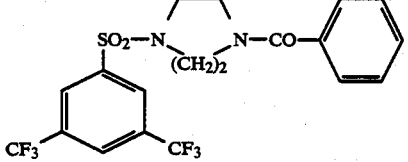 |
| 1 393 | 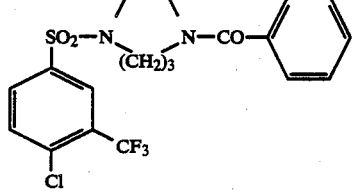 |
| 1 402 | 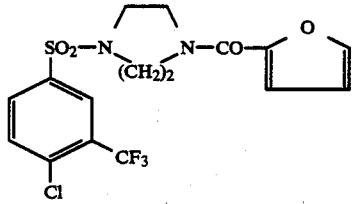 |
| Compound n° | |
|---|---|
| 1 396 | 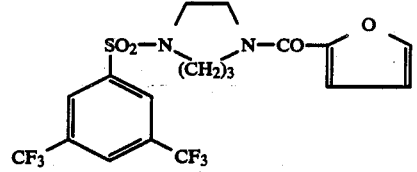 |
| 1 404 | 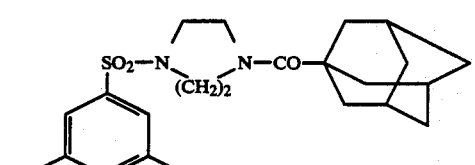 |
| 1 407 | 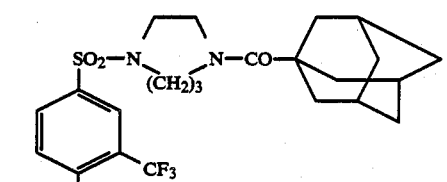 |
A preferred group of medicaments according to the invention is constituted by the compounds of the formulae:
| Compound n° | |
|---|---|
| 1 426 | 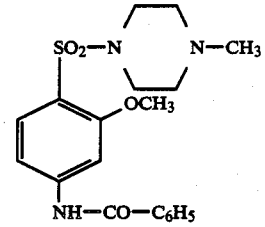 |
| 1 406 | 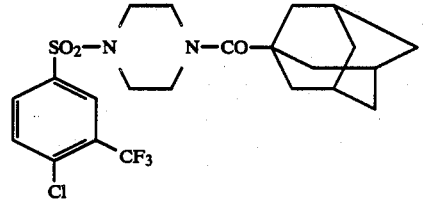 |
| 1 505 | 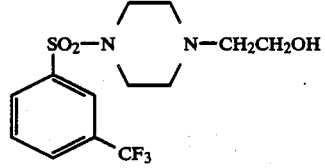 |

-continued

| Compound n° | |
|---|---|
| 1 260 | 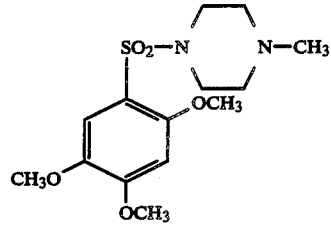 |
| 1 299 | 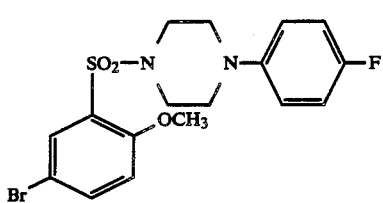 |
| 1 403 | 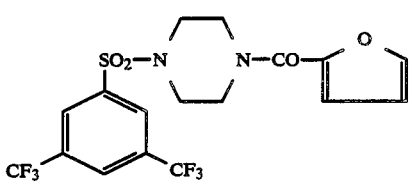 |
| 1 408 | 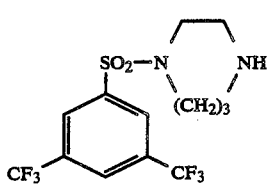 |

The compounds entering into the pharmaceutical compositions (medicaments) constitute novel industrial products, provided that, when n is 2:

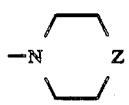

represents a

group, $R_4$ having the meanings indicated above and
either: W or Y represent $CF_3$
or: V represents a group $OR_1$ in which $R_1$ represents an alkyl group of 1 to 4 carbon atoms and one at least of the elements W, X or Y is different from hydrogen.

Forming part of the invention therefore and claimed are the new products corresponding to the above-defined respective groups of medicaments, with the condition, when n is 2, that:

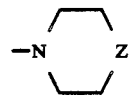

is a piperazino group and the benzenic ring is substituted at the meta position by $CF_3$ or that

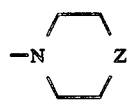

represents a piperazino group and the benzenic ring is at least disubstituted, one of the substituents being an alkoxy group in the ortho position.

Consequently, the new industrial products of the invention correspond to the compounds entering as active substance in the above-defined pharmaceutical compositions, provided that, when n is 2:

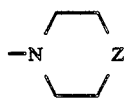

is different from a piperidino and morpholino group and that the benzenic ring is substituted by a meta $CF_3$ or at least disubstituted, one of the substituents being an alkoxy group.

The new industrial products according to the invention correspond to the groups G1bis, G9, G15b, G15c of the above-defined medicaments.

The preferred classes of compounds according to the invention are constituted by the compounds belonging to classes G2 and G3, provided that n is equal to 3.

Other preferred classes of compounds according to the invention are constituted by the compounds belonging to classes G4, G5, G6, G7, provided when n is equal to 2:
either V represents $OR_1$, $R_1$ having the above-indicated meanings, and one at least of the elements W, X and Y is different from hydrogen;
or W represents $CF_3$.

Other preferred classes of compounds according to the invention are constituted by the compounds belonging to the class G8, provided that Z represents $NR_4$, $R_4$ having the above-indicated meanings and
either V represents $OR_1$, $R_1$ having the above-indicated meaning and one at least of the elements W, X and Y is different from hydrogen;
or W represents $CF_3$.

Other preferred classes of compounds according to the invention are constituted by compounds belonging to the class G10, provided that when n is equal to 2, Z represents $NR_4$, $R_4$ having the above-indicated meanings, one at least of the elements W and Y is different from hydrogen.

Other preferred classes according to the invention are constituted by the compounds belonging to classes G11, G12, G13, G13a, G14, G15, G15a, provided that when n is equal to 2, Z represents $NR_4$, $R_4$ having the above-indicated meaning.

The particularly preferred compounds of the invention are those of the formulae:

Compound no
1 242 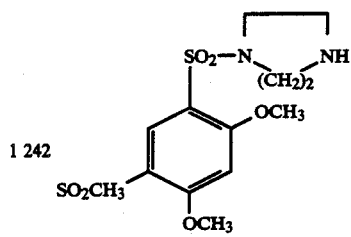
1 265 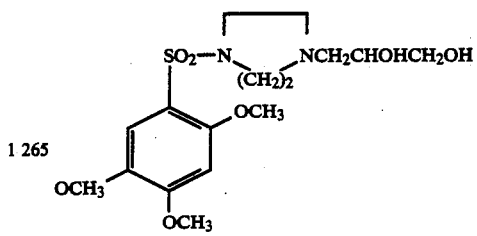
1 270 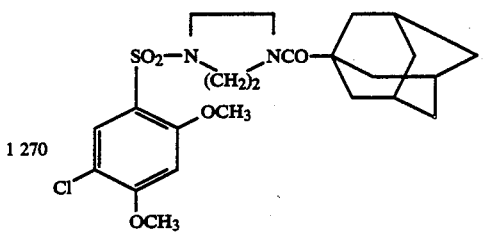
1 301 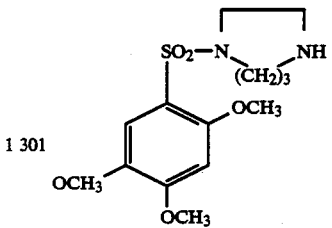
1 304 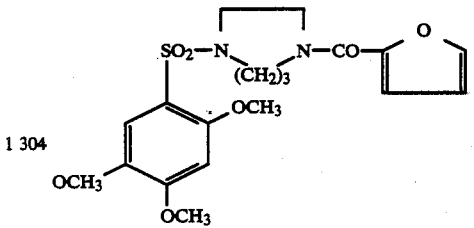
1 306 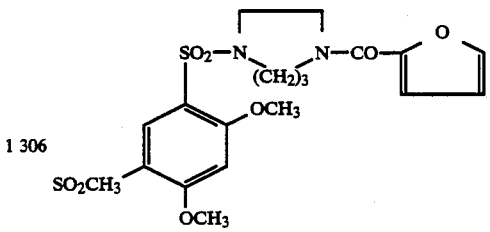
-continued
Compound no
1 334 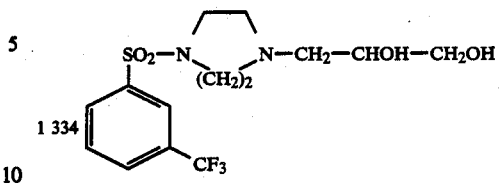
1 400 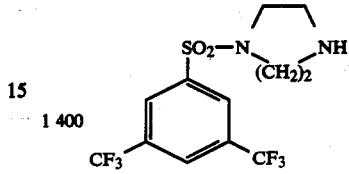
1 339 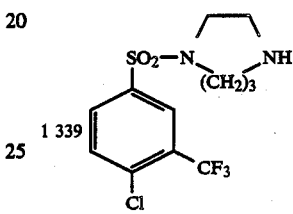
1 389 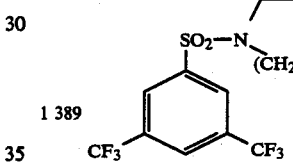
1 397 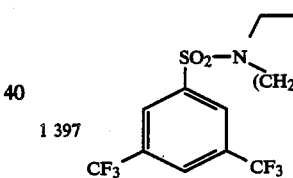
1 390 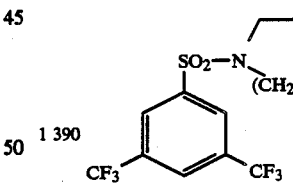
1 336 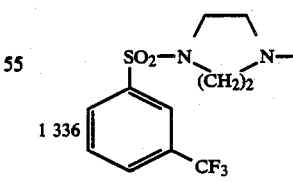
1 392 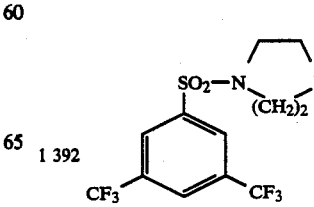

-continued

Compound no

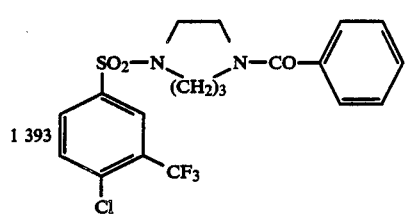
1 393

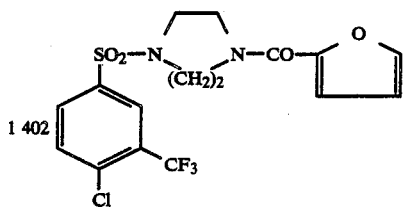
1 402

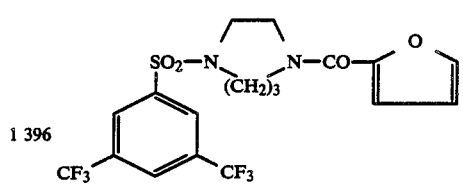
1 396

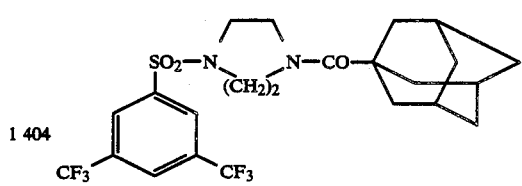
1 404

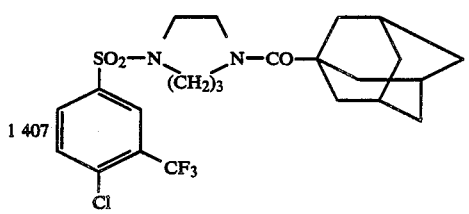
1 407

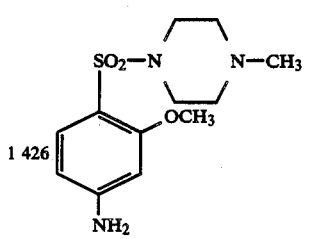
1 426

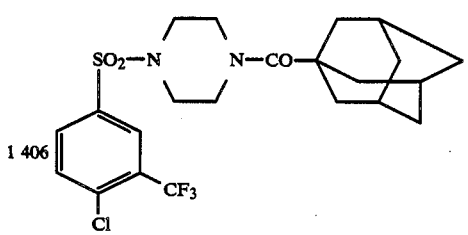
1 406

-continued

Compound no

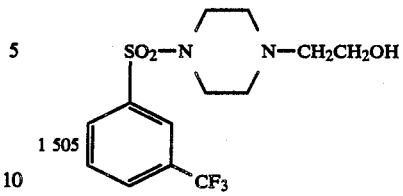
1 505

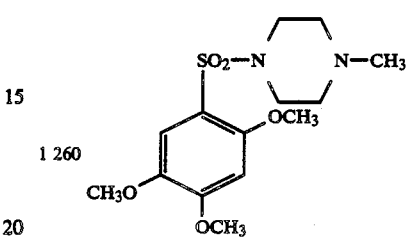
1 260

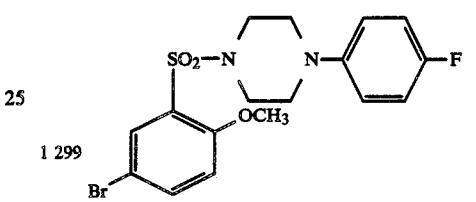
1 299

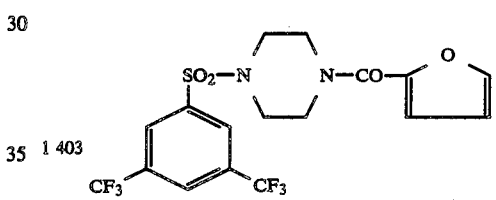
1 403

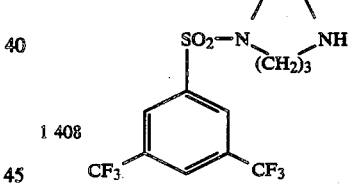
1 408

SYNTHESIS OF THE COMPOUNDS ENTERING INTO THE COMPOSITION OF THE MEDICAMENTS ACCORDING TO THE INVENTION AS WELL AS OF THE NEW COMPOUNDS ACCORDING TO THE INVENTION

In the following, the synthesis of the compounds entering into the composition of medicaments according to the invention, as well as that of the new compounds according to the invention is described.

The compound of formula (I) may be obtained by reaction of the sulfohalogenide of formula (XVI):

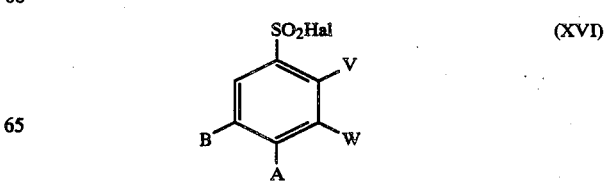
(XVI)

in which V, W have the above-indicated meanings, A and B have the meanings of X and Y, with the exception of NH$_2$, $$\text{NHCR}_2 \atop \underset{O}{\|}$$

and Hal represents a halogen atom, particularly bromine or chlorine, on the compound of formula (XVII):

(XVII)

in which Z and n have the above-indicated meanings.

To carry out this reaction, the compound of formula (XVII) is preferably used, either in excess with respect to the compound of formula (XVI), or by adding a tertiary amine, such as triethylamine, as hydracid acceptor, in order to obtain the compound of formula (I) under unsalted form.

The compounds of formula (I) in which X and Y represent NH$_2$ are obtained by reducing the compound of formula (Ia):

(Ia)

in which A or B represents NO$_2$ by catalytic hydrogenation or by chemical reduction.

The production of compounds of formula (I), in which X or Y represents NHCOR$_2$, can be carried out in a first step by reducing the compound of formula (Ia), as indicated above, to convert the NO$_2$ group corresponding to A or B into NH$_2$, then in a second step by reacting on the compound obtained at the end of the first step, R$_2$COCl or (R$_2$CO)$_2$O, R$_2$ representing an alkyl group of 1 to 4 carbon atoms, to convert the NH$_2$ group into NHCOR$_2$.

To form the compounds according to the invention, it is possible to resort to sulfohalogenides, particularly to sulfochlorides of formula (XVIII):

(XVIII)

in which V, W have the abobe-indicated means, A and B have respectively the meanings of X and Y with the exception of NH$_2$ or $$\text{NHCR}_2 \atop \underset{O}{\|}$$

The preparation of the sulfochlorides is either described in the literature, particularly in French Pat. Nos. 2 313 918 and 2 338 929, or for the sulfochlorides of formula (XIX):

(XIX)

in which R$_5$ and R$_6$ represent, independently of one another, an alkyl radical of 1 to 4 carbon atoms, described in French patent applications Nos. 2 504 528 and 2 504 527 filed on 4/23/1981.

To prepare the formula of compounds (VI):

(VI)

it is possible also to react a sulfochloride of formula (XVIII):

(XVIII)

on the compound of formula (XX):

(XX)

in which R represents an alkyl of 1 to 4 carbon atoms, preferably the ethyl radical, which leads to the compound of formula (XXI):

(XXI)

followed by an alkaline hydrolysis by conventional methods, such as by a strong base such as KOH, and optionally to transform A or B into NH₂, as indicated above, to obtain the compound of formula (VI).

This synthesis will be denoted in the following by synthesis 1.

To prepare the compounds of formula (VI), it is also possible to react the sulfochloride of formula (XVIII):

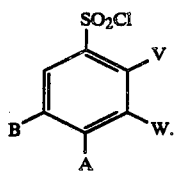

on the compound of formula (XXII):

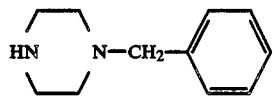

to obtain the compound of formula (XXIII):

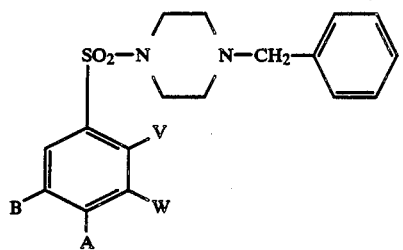

then to eliminate the benzyl radical by conventional methods, such as by hydrogenolysis on palladium and on carbon.

This process may be used preferably when the aromatic ring does not include a halogen.

This synthesis will be denoted in the following by synthesis 2.

To obtain the compound of formula (IV):

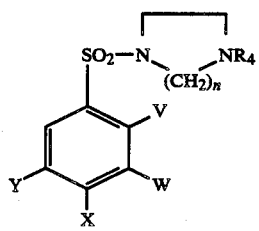

in which R₄ represents
a hydroxyalkyl radical of 2 to 3 carbon atoms;
an aralkyl radical in which the aliphatic chain has 1 to 4 carbon atoms and can include C=O and C—OH groups in which the aroyl group may be unsubstituted or substituted by a halogen atom, by the CF₃ group, by an OR₁ radical, in which R₁ is an alkyl radical having from 1 to 4 carbon atoms;
an aroyl radical of its isoesters unsubstituted or substituted by halogen, by the groups CF₃, by a radical OR₁ in which R₁ is an alcoyl of 1 to 4 carbon atoms; it is possible to manufacture in a first step the compound of formula (XXIV):

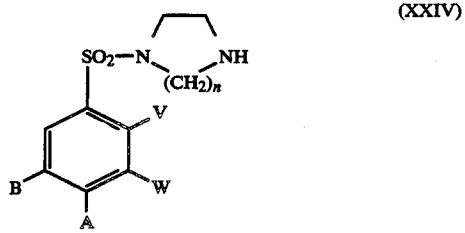

then in a second step to convert this compound of formula (XXIV) into compound of formula (IV) respectively by addition of an epoxy corresponding to the hydroxide, of an aralkyl chloride corresponding to the aralcoyl and of an aroyl chloride corresponding to the aroyl.

The three reaction diagrams below are given by way of example to represent the conversion of a compound of formula (XXIV) into three compounds of formula (IV), in which R₄ represents respectively an aralkyl, an aroyl and an hydroxyalkyl.

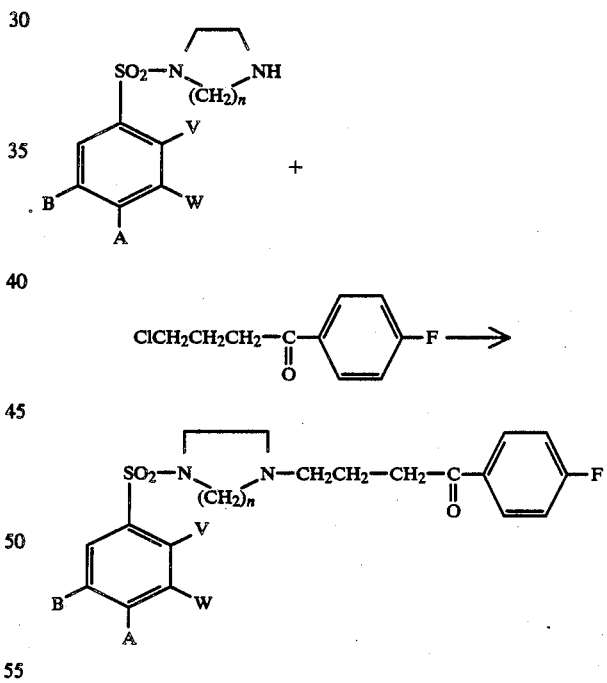

This condensation reaction takes place for 48 hours in the presence of an alkali carbonate, preferably of potassium, and in the presence of a solvent such as the methylisobutylketone or in the other solvent in which the products used are soluble and whose reflux temperature is in the neighbourhood of that of methylisobutylketone.

This reaction is optionally followed by conversion of A or B into NH₂.

This synthesis will be denoted in the following by synthesis 3.

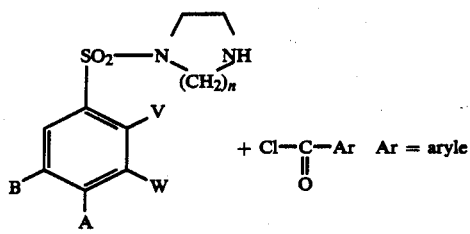

+ Cl—C(=O)—Ar    Ar = aryle

In the cold in the presence of
triethylamine or of any other solvent
which can play the role of H+ ion acceptor →

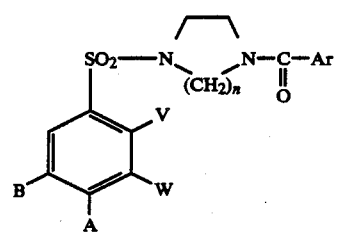

This reaction is if necessary followed by conversion of A or B into NH₂.

This synthesis will be denoted in the following by synthesis 4.

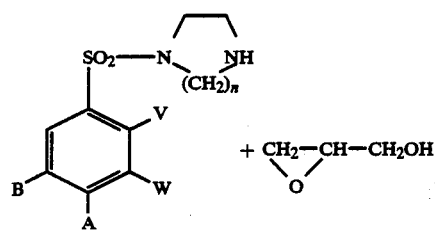

+ CH₂—CH—CH₂OH
  \O/

Heating for about 7 hours to reflux in the presence of CH₃CN or of any other solvent whose reflux temperature is in the neighbourhood of CH₃CN →

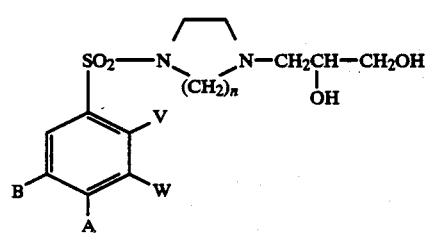

This reaction is if necessary followed by conversion of A or B into NH₂.

This synthesis will be denoted in the following by synthesis 5.

In a preferred embodiment of the process of preparing the compounds according to the invention, the compounds of formula:

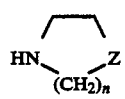

are preferably selected from among:
morpholine,
piperidine,
piperazine,
homopiperazine,
N(2-hydroxy)ethyl piperazine,
N-benzylpiperazine,
1-(4-fluoro phenyl) piperazine,
1-(2,3-dihydroxy propyl) piperazine,
N-methyl piperazine,
N-carbethoxypiperazine,
1-(3-hydroxy propyl) piperazine.

According to a preferred embodiment the process of preparing the compound according to the invention, the compounds of formula:

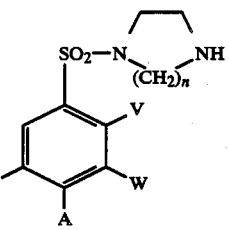

are preferably selected from among:
the sulfochlorides appearing in French Pat. Nos. 2 313 918, 2 338 929, 2 504 528, 2 504 527:
(3,5-ditrifluoromethyl) benzenesulfonyl chloride (see example 1):
5-bromo-2,4-dimethoxy benzenesulfonyl chloride;
5-chloro-2-methoxy-benzenesulfonyl-chloride
5-chloro-2,4-dimethoxy-benzenesulfonyl chloride
2,4-dimethoxy-5-isopropylsulfonyl benzenesulfonyl chloride
2,4-dimethoxy-5-methylsulfonyl-5-benzenesulfonyl-chloride.

In the case of syntheses 3, 4 and 5, the compounds that are reacted with the compounds of formula:

are preferably selected among chloro p. fluorobutyrophenone, benzoyl chloride, adamantoyl chloride, 2,3-epoxy-1-propanol.

To obtain the physiologically acceptable salts of the compounds entering into the composition of medicaments according to the invention, salts are obtained by conventional methods.

The following examples relating to the preparation of a certain number of compounds entering into the composition of medicaments according to the invention serve to illustrate, but are not limiting.

EXAMPLE 1

This example relates to the preparation of 3,5-ditrifluoromethyl) benzenesulfonyl chloride.

46 g (0.2 mole) of 3,5-ditrifluoromethyl aniline were added to a mixture of 150 ml of a solution of hydrochloric acid (d: 1,18) and 50 ml of pure acetic acid by small portions.

The mixture is subjected to stirring then cooled to −5° C. A solution of sodium nitrite (14.5 g in 50 ml of water) is added drop by drop keeping the temperature below 0° C. The addition having ended, it is left in contact with stirring at −5° C., during an hour and then the solution is filtered.

The filtrate is added in portions to the saturated solution of sulfur dioxide in acetic acid (500 ml) containing 11 g of cupric chloride.

The mixture is left under vigorous stirring for 2 h 30, then crushed ice is added until the sulfochloride is precipitated.

The drained precipitate is washed in water then dried under vacuum.

51.4 of product was obtained.

Yield: 82%—M.P.: 38° C.

EXAMPLE 2

1-[5-Bromo 2,4-dimethoxy) benzenesulfonyl morpholine (compound no. 1 216).

To 9.47 g (0.03 mole) of the 5-bromo-2,4-dimethoxy benzenesulfonyl chloride in 50 ml of anhydrous methylene chloride are added, at 0° C. and with stirring 5.22 g (0.06 mole) of morpholine. After four hours of stirring at room temperature, the reaction medium is evaporated to dryness under vacuum. The residue is taken up again with 20 ml of water. The cristals are drained, washed with water to the absence of the $Cl^-$ ion, dried, then recristallized in acetic acid.

8.36 g of product are obtained.

Yield: 76%—M.P.: 186° C.

Analysis: $D_{12}H_{16}BrNO_5S$: 366.23—Calculated C: 39.3; H: 4.4; N: 3.8—Found C: 39.2; H: 4.3; N: 4.0

EXAMPLE 3

1-[(5-Bromo-2,4-dimethoxy) benzenesulfonyl] piperidine (compound no. 1 218)

To 9.47 g (0.03 mole) of 5-bromo-2,4-dimethoxy benzenesulfonyl chloride in 50 ml of anhydrous methylene chloride are added, at 0° C. and with stirring, 5.10 g (0.06 mole) of piperidine. The treatment is the same as in example 2.

8.39 g of product are obtained.

Yield: 77%—M.P.: 149° C.

Analysis: $C_{13}H_{18}BrNO_4S$: 364.26—Calculated C: 42.8; H: 4.9; N: 2.8—Found C: 42.6; H: 4.8; N: 3.8.

EXAMPLE 4

1-[(5-chloro 2-methoxy) benzenesulfonyl] piperazine (compound no. 1 240).

To 43 g (0.5 mole) of piperazine in 250 ml of methylene chloride, are added with the cooling at 0° C., and in 4 hours, a solution of 24.1 g (0.1 mole) of 5-chloro-2-methoxy benzenesulfonyl chloride in 150 ml of anhydrous methylene chloride. The addition having terminated, the reaction mixture is brought back to room temperature and stirring maintained for 6 hours. After evaporation to dryness under vacuum, the residue is taken up again in 200 ml of N hydrochloric acid. The insoluble part is removed. By the addition of N soda, pH is brought to 9. The precipitate is drained, washed with water, then dried. The crystals are recrystallized in benzene.

19.42 g of product are obtained.

Yield: 67%—M.P.: 145° C.

Analysis: $C_{11}H_{15}ClN_2O_3S$: 290.76—Calculated C: 45.4; H: 5.2; N: 9.6—Found C: 45.5; H: 5.1; N: 9.5

EXAMPLE 5

4-[(2-Hydroxy) ethyl] 1-[(5-chloro 2,4-dimethoxy) benzenesulfonyl] piperazine (compound no. 1 296).

To 3.9 g (0.03 mole) of N (2-hydroxy) ethyl piperazine in solution in 30 ml of anhydrous methylene chloride, are added, at 0° C. and with stirring, 10 ml of redistilled triethylamine, then drop by drop, 8.1 g (0.03 mole) of 5-chloro-2,4 dimethoxy benzenesulfonyl chloride in solution in 60 ml of anhydrous methylene chloride. The addition having ended, the reaction mixture is brought back to room temperature and left with stirring for 12 hours. After evaporation to dryness under vacuum, the residue is taken up again in water. The crystals are drained, washed with water until the $Cl^-$ ion is absent then dried under vacuum. They are recrystallized in benzene.

8.12 g of product are obtained.

Yield: 74%—M.P.: 118° C.

Analysis: $C_{14}H_{21}ClN_2O_5S$: 364.86—Calculated C: 46.1; H: 5.8; N: 7.7—Found C: 46.0; H: 5.7; N: 7.6.

EXAMPLE 6

4Benzyl 1-[(2,4-dimethoxy 5-isopropylsulfonyl) benzenesulfonyl] piperazine (compound no. 1 214).

To 3.42 g (0.01 mole) of 2,4 dimethoxy 5-isopropylsulfonyl benzenesulfonyl chloride in 30 ml of anhydrous methylene chloride, are added 3.52 g (0.02 mole) of N-benzylpiperazine in 20 ml of anhydrous methylene chloride, drop by drop, at 0° C. and with stirring. The addition having terminated, the reaction medium is brought back to ordinary temperature and stirred for 12 hours.

After evaporation to dryness under vacuum, the residu is taken up again with 30 ml of water. The crystals are drained, washed with water until the $Cl^-$ is absent, then recrystallized in methanol.

3.57 g of product are obtained.

Yield: 74%—M.P.: 180° C.

Analysis $C_{22}H_{30}H_2O_6S_2$: 482,60—Calculated C: 54.7; H: 6.3; N: 5.8—Found C: 54.5; H: 6.2; N: 5.3.

EXAMPLE 7

[4-(4-Fluoro) phenyl] 1-(2,4-dimethoxy 5-methylsulfonyl) benzenesulfonyl] piperazine (compound no. 1 298).

To 3.15 g (0.01 mole) of 2,4-dimethoxy 5-methylsulfonyl benzenesulfonyl in 30 ml of anhydrous methylene chloride are added 5 ml of redistilled triethylamine then, drop by drop; at 0° C. and with stirring, 1.8 g (0.01 mole of 1(4-fluoro phenyl) piperazine in 10 ml of anhydrous methylene chloride. The addition being terminated, the reaction medium is brought back to room temperature and left under stirring for 12 hours.

After evaporation under vacuum, the residue is taken up again in 20 ml of water. The crystals are drained, washed with water to the $Cl^-$ ion absence, dried, then recrystallized in acetonitrile.

3.24 g of product are obtained.

Yield: 71%—M.P.: 255° C.

Analysis $C_{19}H_{23}FN_2O_6S_2$: 458.53—Calculated C: 49.8; H: 5.1; N: 6.1—Found C: 49.7; H: 5.1; N: 6.1.

The following products have been prepared according to example 2:

Compounds no. 1 202, 1 209, 1 215, 1 216, 1 223, 1 246, 1 247.

The following products were prepared according to example 3:
Compounds no. 1 208, 1 211, 1 218, 1 224, 1 248, 1 249.

The following products were prepared according to example 4:
with piperazine: Compounds no. 1 204, 1 220, 1 240, 1 241, 1 242, 1 243, 1 400, 1 401, 1 504;
with homopiperazine: Compound no. 1 301, 1 302, 1 303, 1 399, 1 408, 1 521.

The following products were prepared according to example 5:
with 1 1-[(2-hydroxy)ethyl]pipeazine: Compounds no. 1 263, 1 264, 1 290, 1 294, 1 296, 1 389, 1 398, 1 505;
with 1-(2,3-dihydroxy propyl)piperazine: Compounds no. 1 265, 1 291, 1 293, 1 295, 1 334, 1 387, 1 397;
with 1 1-(3-hydroxy propyl)piperazine: compound no. 1500.

The following products were prepared according to example 6:
with N-benzylpiperazine: Compounds no. 1 206, 1 213, 1 214, 1 219, 1 222, 1 244, 1 245, 1 335, 1 390, 1 391;
with N-methylpiperazine: Compounds no. 1 260, 1 261, 1 292, 1 424.

The following products were prepared according to example 7:
Compounds no. 1 297, 1 298, 1 299, 1 300, 1 336, 1 353, 1 388.

EXAMPLE 8

4-Carbethoxy 1-[(4-chloro 2,4-dimethoxy)benzenesulfonyl]piperazine.

To 27.1 g (0.1 mole) of 5-chloro 2,4-dimethoxy benzenesulfonyl chloride in solution in 250 ml of anhydrous methylene chloride are added, at 0° C. and with stirring, 50 ml of redistilled triethylamine then drop by drop, a solution of 15.8 g (0.1 mole) of N-carbethoxy piperazine in 100 ml of anhydrous methylene chloride. The addition being terminated, the reaction medium is brought to ambient temperature and left under stirring for 4 hours. After evaporation to dryness under vacuum, the residue is taken up again within 100 ml of water. The crystals are drained, washed with water, dried, then recrystallised in methanol.

33 g of product are obtained.
Yield: 84%—M.P.: 153° C.
Analysis $C_{15}H_{21}ClN_2O_6S$: 392.85—Calculated C: 45.9: H: 5.4; N: 7.1—Found C: 45.7: H: 5.3; N: 7.2.

EXAMPLE 9

1-[(5-Chloro 2,4-dimethoxy)benzenesulfonyl]piperazine (compound no. 1 220)

11.78 g (0.03 mole) of 4-carbethoxy 1-[5-chloro 2,3-dimethoxy)benzenesulfonyl piperazine are placed in solution in 40 g of postashe in 100 ml of water and 20 ml of ethanol, then brought to reflux for 8 hours. After cooling and removal under vacuum of the ethanol, the aqueous phase is extracted twice with 100 ml of ethyl acetate. The organic phase is dried over sodium sulfate then evaporated to dryness under vacuum. The crystals are recrystallised in acetonitrile.

6.44 g of product are obtained.
Yield: 67%—M.P.: 1480C
Analysis $C_{12}H_{17}ClN_2O_4S$: 320.79—Calculated C: 44.9; H: 5.3; N: 8.7—Found C: 44.8; H: 5.3; N: 8.7.

The following products were prepared according to examples 8 and 9: Compounds no. 1 220, 1 241, 1 243.

EXAMPLE 10

1-[(2,4-Dimethoxy 5-methylsulfonyl)benzenesulfonyl]piperazine (compound no. 1 242).

4.54 g (0.01 mole) of 4-benzyl 1-2,4-dimethoxy 5-methylsulfonyl)benzenesulfonyl]piperazine are placed in solution in 150 ml of absolute ethanol and hydrogenated at ordinary pressure in the presence of 0.5 g of palladium on carbon at 50° C., for 3 hours. After the theoretical hydrogen absorption,the catalyst is eliminated by filtration. The evaporation of the ethanolic phase results in 4 g of crystals which can be recrystallised in methanol.

4 g of product are obtained.
Yield: 95%—M.P.: 140° C.
Analysis $C_{13}H_{20}N_2O_6S_2$: 364.43—Calculated C: 42.8; H: 5.5; N: 7.7—Found C: 42.4: H: 5.4; N: 7.5.

The following products were prepared according to example 10: Compounds no. 1 220, 1 243, 1 204.

EXAMPLE 11

4-(4-Fluoro butyrophenone)-1-[(5-chloro-2,4-dimethoxybenzenesulfonyl]piperazine (compound no. 1 251).

To 4.8 g (0.015 mole) of 1-[(5-chloro 2,4-dimethobenzenesulfonyl]piperazine in 80 ml of anhydrous methylisobutylketone are added 10 g of anhydric potassium carbonate, then drop by drop, 8.03 g (0.040 mole) of chloro p. fluorobutyrophenone. The reaction medium is brought to reflux for 48 hours. After evaporation under vacuum, the residu is taken up again in 100 ml of water, then extracted twice by 100 ml of ethyl acetate.

The organic phase dried on sodium sulfate is evaporated to dryness on the vacuum, the residue is chromatographed on silica with the chloroform eluant to give 4 g of product which is recrystallised in ethanol.

1.88 g of product are obtained.
Yield: 26%—M.P.: 120° C.
Analysis $C_{22}H_{26}ClFN_2O_5S$: 484.97—Calculated C: 54.5; H: 5.4; N: 5.8—Found C: 54.5; H: 5.4; N: 5.6.

In the same way, a 4-(4'-fluoro butyrophenone) 1-[(5-chloro 2-methoxy)benzenesulfonyl]piperazine is prepared.

EXAMPLE 12

4-Benzoyl 1-[5-chloro 2,4-dimethoxy)benzenesulfonyl]piperazine (compound no. 1 272).

To 4.8 g (0.015 mole) of 1-[(5-chloro 2,4-dimethoxy)-benzenesulfonyl]piperazine in 40 ml of anhydrous methylene chloride, are added, at 0° C. and with stirring 10 ml of redistilled triethylamine then 2.11 g (0.015 mole) of redistilled benzoyl chloride, drop by drop, in solution in 10 ml of methylene chloride. The addition terminated, the reaction medium is brought back to ambient temperature and left under stirring for 12 hours.

After evaporation to dryness under vacuum, the residue is taken up again in 20 ml of water, the crystals are drained, washed with water, dried then recrystallised in ethanol.

4.22 g of product are obtained.
Yield: 66%—M.P.: 210° C.
Analysis $C_{19}H_{21}ClN_2O_5S$: 424.89—Calculated C: 53.7; H: 5.0; N: 6.6—Found C: 53.7; H: 5.0 N: 6.6.

The following products were prepared according to example 12:
with benzoyl chloride: Compounds no. 1 273, 1 308, 1 392, 1 393, 1 394, 1 502;

with 1-adamantoyl chloride: Compounds no. 1 270, 1 271, 1 305, 1 307, 1 395, 1 404, 1 406, 1 407, 1 503.

with 2-furoyl chloride: Compound no. 1 274, 1 275, 1 304, 1 306, 1 396, 1 402, 1 403, 1 405.

EXAMPLE 13

4-(2.3-dihydroxy propyl) 1-[(3,5-ditrifluoromethyl)-benzenesulfonyl]homopiperazine (compound no. 1 488).

To 3.76 g (0.01 mole) of 1-[(3,5-ditrifluoromethyl)-benzenesulfonyl]homopiperazine in 30 ml of acetonitrile are added with stirring 0.74 g (0.01 mole) of 2.3-epoxy 1-propanol in a solution in 5 ml of acetonitrile. The reaction medium is brought to reflux for 8 hours. After evaporation to drying under vacuum, a crystalline residue is obtained which is chromatographed on the silica column with a chloroform of 90-methanol 10 eluant. The product is recrystallised in ethyl acetate.

2.2 g of product are obtained.

Yield: 49%—M.P.: 128° C.

Analysis $C_{16}H_{20}F_6N_2O_4S$: 450.414—Calculated C: 42.7; H: 4.5; N: 6.2—Found C: 42.5 h: 4.4; N: 6.4.

In the same manner, 4-(2.3-dihydroxy propyl) 1-[3.5 ditrifluoromethyl)benzenesulfonyl piperazine (compound no. 1 397) is prepared.

EXAMPLE 14

1-[Amino 2-methoxy)benzenesulfonyl]4-methyl piperazine (compound no. 1 425).

4.6 g (0.015 mole) of 1-[(2-methoxy 4-nitro)benzenesulfonyl]4-methyl piperazine in solution in 200 ml of anhydrous ethanol are hydrogenated at 20° C. and at ordinary pressure in the presence of Raney nickel. After theoretical absorption of hydrogen, the catalyst is removed by filtration.

The filtrate evaporated to dryniss gives a crystalline residue. The product is recrystallised in a minimum of ethanol.

4 g of product are obtained.

Yield: 93%—M.P.: 174° C.

Analysis $C_{12}H_{19}N_3O_3S$: 285.369—Calculated C: 50.5; H: 6.7; N: 14.7—Found C: 50.4; H: 6.6; N: 14.8.

In the same manner, 1'1-[(4-amino 5-chloro 2-methoxy)benzenesulfonyl]4-methyl piperazine (compound no. 1 427) is prepared.

EXAMPLE 15

1-[(4-benzamido 2-methoxy)benzenesulfonyl]4-methylpiperazine (compound no. 1 426).

To 1.42 g (0.005 mole) of 1-[(4-amino-2-methoxy)benzenesulfonyl]4-methyl piperazine in 10 ml of anhydrous methylene chloride are added at 0° C. under stirring, 4 ml of triethylamine, then 0.8 g of benzoyl chloride in solution in 5 ml of anhydrous methylene chloride.

The reaction medium brought back to room temperature is stirred for 12 hours then evaporated to dryness under vacuum. The residue is taken up again in 10 ml of water, then extracted with 2×25 ml of ethyl acetate. The organic phase dried over $Na_2SO_4$, then evaporated under vacuum gives a solid residue which is purified by chromatography on silica with an eluant of ($CHCl_3$ 95, MeOH 5l).

The product is recrystallised in ethyl acetate.

MP.: 147° C.

Analysis $C_{19}H_{23}N_3O_4S$: 389.478—Calculated C: 58.6; H: 5.9; N: 10.8—Found C: 58.3; H: 5.9; N: 10.5.

EXAMPLE 16

1-[(4-Acetamido 5-chloro 2-methoxy)benzenesulfonyl]4-methyl piperazine (compound no. 1 428).

1.6 g (0.005 mole) of 1-[(4-amino 5-chloro 2-methoxy)benzenesulfonyl]4-methyl piperazine in 3 ml of distilled acetic anhydride and a drop of concentrated sulfuric acid are brought to reflux for 3 hours. After cooling, there is added 10 ml of water, then 2N soda to bring it to pH 10. It is extracted with two lots of 50 ml of ethyl acetate. The organic phase is dried over sodium sulfate, then evaporated to dryness under vacuum. The residue is recrystallised in ethyl acetate.

MP.: 172° C.

Analysis $C_{14}H_{20}ClN_3O_4S$: 361.856—Calculated C: 46.5; H: 5.6; N: 11.6—Found C: 46.2; H: 5.4: N: 11.5

The products of examples 4 to 16 as well as the products prepared according to examples 4 to 16, mentioned above, are novel industrial products.

Table I below indicates for each of the compounds according to the invention and of the compounds which enter into the preparation of medicaments according to the invention and which can be prepared as indicated above, the formula, the molecular weight, the melting point and the yield.

TABLE I

| Compound N° | V | W | X | Y | n | Z | Empirical formula | M. W. | M.P. °C. | Yield |
|---|---|---|---|---|---|---|---|---|---|---|
| 1202 | OCH3 | H | OCH3 | OCH3 | 2 | O | C13H19NO6S | 317,37 | 104 | 81 |
| 1209 | OCH3 | H | NO2 | Cl | 2 | O | C11H13ClN2O6S | 336,75 | 179 | 66 |
| 1215 | OCH3 | H | OCH3 | SO2—iC3H7 | 2 | O | C15H23NO7S2 | 393,47 | 226 | 60 |
| 1216 | OCH3 | H | OCH3 | Br | 2 | O | C12H16BrNO5S | 366,23 | 186 | 76 |
| 1223 | OCH3 | H | OCH3 | Cl | 2 | O | C12H16ClNO5S | 321,77 | 186 | 74 |
| 1246 | OCH3 | H | OCH3 | H | 2 | O | C12H17NO5S | 287,33 | 124 | 74 |
| 1247 | OCH3 | H | H | Cl | 2 | O | C11H14ClNO4S | 291,75 | 136 | 83 |
| 1208 | OCH3 | H | NO2 | Cl | 2 | CH2 | C12H15ClN2O5S | 334,77 | 184 | 89 |
| 1211 | OCH3 | H | OCH3 | SO2—CH3 | 2 | CH2 | C14H21NO6S2 | 363,45 | 190 | 74 |
| 1218 | OCH3 | H | OCH3 | Br | 2 | CH2 | C13H18BrNO4S | 364,26 | 149 | 73 |
| 1224 | OCH3 | H | OCH3 | Cl | 2 | CH2 | C13H18ClNO4S | 319,80 | 152 | 77 |
| 1248 | OCH3 | H | OCH3 | H | 2 | CH2 | C13H19NO4S | 285,36 | 105 | 86 |
| 1249 | OCH3 | H | H | Cl | 2 | CH2 | C12H16ClNO3S | 289,78 | 86 | 86 |
| 1204 | OCH3 | H | OCH3 | H | 2 | NH | C12H16N2O4S, HBr | 365,25 | 102 | 99 |
| 1220 | OCH3 | H | OCH3 | SO2—CH3 | 2 | NH | C12H17ClN2O4S | 320,79 | 149 | 65 |
| 1240 | OCH3 | H | OCH3 | Br | 2 | NH | C11H15ClN2O3S | 290,76 | 145 | 67 |
| 1241 | OCH3 | H | NO2 | Cl | 2 | NH | C11H14ClN3O5S | 335,76 | 162 | 51 |
| 1242 | OCH3 | H | OCH3 | SO2—CH3 | 2 | NH | C13H20N2O5S2 | 364,43 | 140 | 95 |
| 1243 | OCH3 | H | OCH3 | OCH3 | 2 | NH | C13H20N2O5S | 316,37 | 108 | 31 |
| 1400 | OCH3 | CF3 | H | CF3 | 2 | NH | C12H12F6N2O2S, HCl | 416,77 | 105 | 68 |
| 1401 | H | CF3 | Cl | H | 2 | NH | C11H12ClF3N2O2S | 328,75 | 118 | 76 |
| 1301 | OCH3 | H | OCH3 | OCH3 | 3 | NH | C14H22N2O5S | 330,40 | 99 | 50 |
| 1302 | OCH3 | H | OCH3 | SO2—CH3 | 3 | NH | C14H22N2O6S2 | 378,47 | 154 | 49 |
| 1303 | OCH3 | H | OCH3 | Cl | 3 | NH | C13H19ClN2O4S | 334,83 | 138 | 78 |
| 1408 | H | CF3 | OCH3 | CF3 | 3 | NH | C13H14F6N2O2S | 376,33 | 89 | 78 |
| 1399 | H | CF3 | Cl | CF3 | 2 | NH | C12H14ClF3N2O2S, HCl | 379,24 | 256 | 46 |
| 1260 | OCH3 | H | OCH3 | H | 2 | N—CH3 | C14H22N2O5S | 330,40 | 114 | 66 |
| 1261 | OCH3 | H | OCH3 | Cl | 2 | N—CH3 | C13H19ClN2O4S | 334,82 | 131 | 70 |
| 1292 | OCH3 | H | NO2 | Cl | 2 | N—CH3 | C13H19ClN3O5S | 349,79 | 135 | 82 |
| 1263 | OCH3 | H | OCH3 | Cl | 3 | N—CH3 | C13H19ClN2O4S | 334,82 | 111 | 72 |
| 1264 | OCH3 | H | OCH3 | OCH3 | 2 | N—CH2—CH2OH | C15H24N2O6S | 360,43 | 103 | 65 |
| 1290 | OCH3 | H | OCH3 | SO2—CH3 | 2 | N—CH2—CH2OH | C15H24N2O7S2 | 408,50 | 122 | 72 |
| 1296 | OCH3 | H | OCH3 | Cl | 2 | N—CH2—CH2OH | C14H21ClN2O5S | 364,86 | 118 | 74 |
| 1389 | H | CF3 | H | CF3 | 2 | N—CH2—CH2OH | C14H16F6N2O3S | 406,34 | 84 | 41 |
| 1398 | H | CF3 | Cl | CF3 | 2 | N—CH2—CH2OH | C13H16ClF3N2O5S | 372,79 | 87 | 55 |
| 1262 | OCH3 | H | OCH3 | Cl | 2 | N—CH2—CHOH—CH2OH | C14H21ClN2O5S | 364,85 | 115 | 77 |
| 1265 | OCH3 | H | NO2 | Cl | 2 | N—CH2—CHOH—CH2OH | C16H26N2O7S | 390,46 | 158 | 62 |
| 1291 | OCH3 | H | OCH3 | Cl | 2 | N—CH2—CHOH—CH2OH | C14H20ClN3O7S | 409,68 | 174 | 33 |
| 1293 | OCH3 | H | OCH3 | SO2—CH3 | 2 | N—CH2—CHOH—CH2OH | C16H26N2O8S2 | 434,52 | 205 | 31 |
| 1295 | OCH3 | H | OCH3 | Cl | 2 | N—CH2—CHOH-CH2OH | C15H23ClN2O6S | 394,89 | 118 | 69 |
| 1334 | OCH3 | H | OCH3 | H | 2 | N—CH2—CHOH—CH2OH | C14H19F3N2O4S, CH3SO3H | 464,49 | 200 | 43 |
| 1387 | H | CF3 | H | CF3 | 2 | N—CH2—CHOH—CH2OH | C14H18ClF3N2O4S | 402,82 | 119 | 41 |
| 1397 | H | CF3 | Cl | CF3 | 2 | N—CH2—CHOH—CH2OH | C14H18F6N2O4S | 436,37 | 104 | 31 |
| 1206 | OCH3 | H | NO2 | Cl | 2 | N—CH2—C6H5 | C18H20ClN3O5S | 425,89 | 140 | 45 |
| 1213 | OCH3 | H | OCH3 | SO2—CH3 | 2 | N—CH2—C6H5 | C20H26N2O6S2 | 454,55 | 165 | 59 |
| 1214 | OCH3 | H | OCH3 | SO2—iC3H7 | 2 | N—CH2—C6H5 | C22H30N2O6S2 | 482,60 | 180 | 74 |
| 1219 | OCH3 | H | OCH3 | Br | 2 | N—CH2—C6H5 | C19H23BrN2O4S | 455,37 | 164 | 73 |
| 1222 | OCH3 | H | OCH3 | Cl | 2 | N—CH2—C6H5 | C19H23ClN2O4S | 410,92 | 150 | 76 |
| 1244 | OCH3 | H | OCH3 | H | 2 | N—CH2—C6H5 | C19H24N2O4S | 376,47 | 138 | 89 |
| 1245 | OCH3 | H | H | Cl | 2 | N—CH2—C6H5 | C18H21ClN2O3S | 380,89 | 104 | 46 |

TABLE I-continued

| Compound N° | V | W | X | Y | n | Z | Empirical formula | M.W. | M.P. °C. | Yield |
|---|---|---|---|---|---|---|---|---|---|---|
| 1335 | H | CF$_3$ | H | H | 2 | N—CH$_2$—C$_6$H$_5$ | C$_{18}$H$_{19}$F$_3$N$_2$O$_2$S, HCl | 420,89 | 250 | 83 |
| 1390 | H | CF$_3$ | H | CF$_3$ | 2 | N—CH$_2$—C$_6$H$_5$ | C$_{19}$H$_{18}$F$_6$N$_2$O$_2$S | 452,43 | 85 | 67 |
| 1391 | H | CF$_3$ | Cl | H | 2 | N—CH$_2$—C$_6$H$_5$ | C$_{18}$H$_{18}$ClF$_3$N$_2$O$_2$S | 418,88 | 124 | 63 |
| 1251 | OCH$_3$ | H | OCH$_3$ | Cl | 2 |  N—(CH$_2$)$_3$—CO—⌬—F | C$_{22}$H$_{26}$ClFN$_2$O$_5$S | 484,97 | 120 | 26 |
| 1269 | OCH$_3$ | H | H | Cl | 2 |  N—(CH$_2$)$_3$—CO—⌬—F | C$_{21}$H$_{24}$ClFN$_2$O$_4$S, HCl | 491,41 | 190 | 10 |
| 1297 | OCH$_3$ | H | OCH$_3$ | OCH$_3$ | 2 |  N—⌬—F | C$_{19}$H$_{23}$FN$_2$O$_5$S | 410,47 | 188 | 83 |
| 1298 | OCH$_3$ | H | OCH$_3$ | SO$_2$—CH$_3$ | 2 |  N—⌬—F | C$_{19}$H$_{23}$FN$_2$O$_6$S$_2$ | 458,53 | 255 | 71 |
| 1299 | OCH$_3$ | H | H | Br | 2 |  N—⌬—F | C$_{17}$H$_{18}$BrFN$_2$O$_3$S | 429,32 | 125 | 58 |
| 1300 | OCH$_3$ | H | OCH$_3$ | Cl | 2 |  N—⌬—F | C$_{18}$H$_{20}$ClFN$_2$O$_4$S | 414,90 | 170 | 64 |
| 1336 | H | CF$_3$ | H | H | 2 |  N—⌬—F | C$_{17}$H$_{16}$F$_4$N$_2$O$_2$S | 388,39 | 100 | 75 |
| 1353 | OCH$_3$ | H | H | NO$_2$ | 2 |  N—⌬—F | C$_{17}$H$_{18}$FN$_3$O$_5$S | 395,42 | 205 | 73 |

TABLE I-continued
| Compound N° | V | W | X | Y | n | Z | Empirical formula | M.W. | M.P. °C. | Yield |
|---|---|---|---|---|---|---|---|---|---|---|
| 1388 | H | CF$_3$ | H | CF$_3$ | 2 |  | C$_{18}$H$_{15}$FN$_2$O$_2$S | 456,40 | 152 | 62 |
| 1272 | OCH$_3$ | H | OCH$_3$ | Cl | 2 | 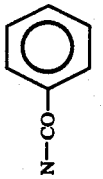 | C$_{19}$H$_{21}$ClN$_2$O$_5$S | 424,89 | 210 | 66 |
| 1273 | OCH$_3$ | H | OCH$_3$ | H | 2 | 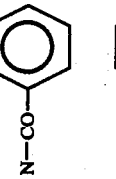 | C$_{19}$H$_{22}$N$_2$O$_5$S | 390,45 | 171 | 68 |
| 1392 | H | CF$_3$ | H | CF$_3$ | 2 | 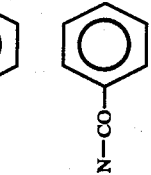 | C$_{19}$H$_{16}$F$_6$N$_2$O$_3$S | 466,42 | 164 | 45 |
| 1308 | OCH$_3$ | H | OCH$_3$ | Cl | 3 |  | C$_{20}$H$_{23}$ClN$_2$O$_5$S | 438,94 | 210 | 60 |
| 1393 | H | CF$_3$ | Cl | H | 3 | 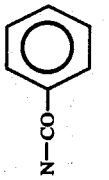 | C$_{19}$H$_{18}$ClF$_3$N$_2$O$_3$S | 446,89 | 95 | 76 |
| 1394 | H | CF$_3$ | H | CF$_3$ | 3 |  | C$_{20}$H$_{18}$F$_6$N$_2$O$_3$S | 480,44 | 120 | 35 |
| 1274 | OCH$_3$ | H | OCH$_3$ | Cl | 2 |  | C$_{17}$H$_{19}$ClN$_2$O$_6$S | 414,86 | 138 | 81 |

TABLE I-continued

| Compound N° | V | W | X | Y | n | Z | Empirical formula | M.W. | M.P. °C. | Yield |
|---|---|---|---|---|---|---|---|---|---|---|
| 1275 | OCH$_3$ | H | H | Cl | 2 |  | C$_{16}$H$_{17}$ClN$_2$O$_5$S | 384,82 | 131 | 56 |
| 1402 | H | CF$_3$ | Cl | H | 2 |  | C$_{16}$H$_{14}$ClF$_3$N$_2$O$_4$S | 422,82 | 163 | 71 |
| 1403 | H | CF$_3$ | H | CF$_3$ | 2 |  | C$_{17}$H$_{14}$F$_6$N$_2$O$_4$S | 456,38 | 138 | 62 |
| 1304 | OCH$_3$ | H | OCH$_3$ | OCH$_3$ | 3 |  | C$_{19}$H$_{24}$N$_2$O$_7$S | 424,47 | 175 | 75 |
| 1306 | OCH$_3$ | H | OCH$_3$ | SO$_2$—CH$_3$ | 3 | 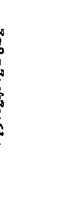 | C$_{19}$H$_{24}$N$_2$O$_8$S$_2$ | 472,53 | 187 | 73 |
| 1396 | H | CF$_3$ | H | CF$_3$ | 3 |  | C$_{18}$H$_{16}$F$_6$N$_2$O$_4$S | 470,40 | 130 | 34 |
| 1405 | H | CF$_3$ | Cl | H | 3 |  | C$_{17}$H$_{16}$ClF$_3$N$_2$O$_4$S | 436,85 | 104 | 75 |
| 1270 | OCH$_3$ | H | OCH$_3$ | Cl | 2 |  | C$_{23}$H$_{31}$ClN$_2$O$_5$S | 483,02 | 266 | 88 |
| 1271 | OCH$_3$ | H | OCH$_3$ | H | 2 |  | C$_{23}$H$_{32}$N$_2$O$_5$S | 448,58 | 188 | 60 |

TABLE I-continued

| Compound N° | V | W | X | Y | n | Z | Empirical formula | M.W. | M.P. °C. | Yield |
|---|---|---|---|---|---|---|---|---|---|---|
| 1404 | H | CF$_3$ | H | CF$_3$ | 2 | (adamantyl)N—CO | C$_{23}$H$_{26}$F$_6$N$_2$O$_3$S | 524.54 | 183 | 54 |
| 1406 | H | CF$_3$ | Cl | H | 2 | (adamantyl)N—CO | C$_{22}$H$_{26}$ClF$_3$N$_2$O$_3$S | 490.99 | 118 | 57 |
| 1305 | OCH$_3$ | H | OCH$_3$ | OCH$_3$ | 3 | (adamantyl)N—CO | C$_{25}$H$_{36}$N$_2$O$_6$S | 492.63 | 162 | 61 |
| 1307 | OCH$_3$ | H | OCH$_3$ | SO$_2$—CH$_3$ | 3 | (adamantyl)N—CO | C$_{24}$H$_{33}$ClN$_2$O$_5$S | 497.05 | 169 | 60 |
| 1395 | H | CF$_3$ | H | CF$_3$ | 3 | (adamantyl)N—CO | C$_{24}$H$_{28}$F$_6$N$_2$O$_3$S | 538.57 | 148 | 27 |
| 1407 | H | CF$_3$ | Cl | H | 3 | (adamantyl)N—CO | C$_{23}$H$_{28}$ClF$_3$N$_2$O$_3$S | 505.01 | 145 | 57 |
| 1424 | OCH$_3$ | H | NO$_2$ | H | 2 | N—CH$_3$ | C$_{12}$H$_{17}$N$_3$O$_5$S | 315.35 | 110 | 72 |
| 1425 | OCH$_3$ | H | NH$_2$ | H | 2 | N—CH$_3$ | C$_{12}$H$_{19}$N$_3$O$_3$S | 285.37 | 174 | 93 |
| 1426 | OCH$_3$ | H | NH—CO—C$_6$H$_5$ | H | 2 | N—CH$_3$ | C$_{19}$H$_{23}$N$_3$O$_4$S | 389.48 | 147 | 40 |
| 1427 | OCH$_3$ | H | NH$_2$ | Cl | 2 | N—CH$_3$ | C$_{12}$H$_{18}$ClN$_3$O$_4$S | 319.81 | 162 | 90 |
| 1428 | OCH$_3$ | H | NHCOCH$_3$ | Cl | 2 | N—CH$_3$ | C$_{14}$H$_{20}$ClN$_3$O$_4$S | 361.86 | 172 | 30 |
| 1488 | H | CF$_3$ | H | CF$_3$ | 3 | NCH$_2$CHOHCH$_2$OH | C$_{16}$H$_{20}$F$_6$N$_2$O$_5$S | 450.414 | 128 | 48 |
| 1500 | H | CF$_3$ | H | H | 2 | NCH$_2$CH$_2$OH | C$_{14}$H$_{19}$F$_3$N$_2$O$_3$S | 352.375 | 87 | 30 |

TABLE I-continued

| Compound N° | V | W | X | Y | n | Z | Empirical formula | M.W. | M.P. °C. | Yield |
|---|---|---|---|---|---|---|---|---|---|---|
| 1502 | H | CF$_3$ | H | H | 2 | ![benzoyl]N-C(=O)-C$_6$H$_5$ | C$_{18}$H$_{17}$F$_3$N$_2$O$_3$S | 398.403 | 118 | 65 |
| 1503 | H | CF$_3$ | H | H | 2 | ![adamantoyl]N-C(=O)-adamantyl | C$_{22}$H$_{27}$F$_3$N$_2$O$_3$S | 456.527 | 170 | 61 |
| 1504 | H | CF$_3$ | H | H | 2 | NH | C$_{11}$H$_{13}$F$_3$N$_2$O$_2$S | 294.295 | 65 | 73 |
| 1505 | H | CF$_3$ | H | H | 2 | N—CH$_2$CH$_2$OH | C$_{13}$H$_{17}$F$_3$N$_2$O$_3$S | 338.348 | 95 | 82 |
| 1521 | H | CF$_3$ | H | H | 3 | NH | C$_{12}$H$_{15}$F$_3$N$_2$O$_2$S | 308.330 | 110 | 40 |

The above-indicated chemical compounds as well as their physiologically acceptable organic or inorganic salts may enter, as active substances, into the preparation of medicaments presenting a group of therapeutic and pharmacological properties of great value.

The medicaments according to the invention exert an action on the central nervous system, particularly anxiolytic.

These pharmacological properties have been studied by taking as a reference substance trimetozine (marketed under the trademark OPALENE).

The medicaments according to the invention are advantageously used in the treatment of neurotic disorders, with anxiety, irritability and character troubles.

The compounds which enter into the medicaments according to the invention are for this purpose conditioned with the traditional excipients and adjuvants, particularly those used for oral administration such as tablets, powders, capsules, drinkable ampoulae or ampoulae for administration in injectable solution form, or suppositories.

The administration of medicaments containing compounds according to the invention is effected preferably orally and the doses of said administered compounds are preferably comprised between 1 and 1000 mg, and particularly between 5 and 250 mg/day, according to the method of administration.

An example of pharmaceutical composition according to the invention is constituted by a tablet or a capsule containing 5 or 10 mg of one at least of the above-defined compounds.

By way of examples, various tests for the establishment of the pharmacological properties of the compounds according to the invention are reported hereafter.

STUDY OF TOXICITY

The results relating to the toxicity are reported below in the following table II.

TABLE II

| Compound n° | Route | Doses mg/kg | | | Number of doses | Number of mice |
|---|---|---|---|---|---|---|
| | | $LD_0$ | $LD_{50}$ | $LD_{100}$ | | |
| 1 243 | IV | 200 | 200 | 325 | 8 | 80 |
| 1 292 | IP | 400 | 650 | 1 000 | 7 | 70 |
| 1 295 | IP | 600 | 820 | 1 000 | 9 | 90 |
| 1 245 | IP | >2 000 | >2 000 | >2 000 | 3 | 30 |
| 1 298 | IP | >2 000 | >2 000 | >2 000 | 3 | 30 |

For the compounds no. 1 393 and 1 402, the $LD_0$ is superior to 2 000 mg/kg by oral route.

For compounds no. 1 400 and 1 427, the $LD_0$ is respectively in the order of 250 and 500 mg/kg, whilst the $LD_{50}$ is respectively of about 700 and about 800 mg/kg.

The following compounds: no. 1 393, 1 400, 1 402, 1 427, 1 243, 1 292, 1 295, 1 245, 1 298 have shown that the ratio between the effective dose and the toxicity is satisfactory, which must lead to a satisfactory therapeutic index.

STUDY OF THE PROPERTIES OF THE COMPOUNDS ACCORDING TO THE INVENTION IN THE 4 PLATES TEST

The test with 4 plates or trial of suppressive conditioning was described by SLOTNIK and JARVID (Science, 1966, 154, 1 207–1 208) in 1968, then developed by ARON-SAMUEL (These Doctorat Etat Médecine Paris 1970).

By means of this test, this author had studied substances belonging to various families of psychotropes and only tranquillizers (minor tranquillizers) have affected the behavior of mice at doses inactive on the motility. According to SIMON and COLONNA, it is an excellent method of sorting tranquillizing substances ("for better knowing and prescribing the psychotropic agents", PIL Ed. Paris 1982).

MATERIAL AND METHOD

Active principle

The method is based on the attenuation or suppression of the anxiety state induced by electric shocks on movement of the animals (mice) into a special enclosure.

The anxiolytic effect is manifested by an increase in movements at doses not affecting motility.

Animals

Swiss male mice derived from CERJ (53680 Le Genest) of a body weight of 20–22 g, acclimatized for 8 days in the animal section of the laboratory. For each dose, the groups are of 15 animals which have not undergone the test.

Equipment

The apparatus was of the Apelex type.

It is composed of a parallelepipedic box of white plastic material, provided with a lid of transparent plexiglas, mobile by means of two hinges. The floor, which is rectangular, is constituted by four plates of conductive metal of which the distance between one another and the walls of the box is of 0.5 cm.

These plates are connected to an Apelex impulse generator. The potential difference when there is no impulse is, nil between two plates on a diagonal and is of 180 Volts between two adjacent plates. A trigger enables that a constant electrical current pulse be sent (of 0 to 2 milliamperes) for a selected time (from 0.1 to 5 seconds).

Procedure

The operation is carried out in a silent area at constant temperature, the experimenter overlooking the box so that he can follow all the movements of the mice placed on one of the plates. The trigger is spaced away from the box in order that the noice does not modify the behavior of the animal.

For each animal, the experiment is carried out according to the following modalities:

preliminary exploration of 15 seconds, without electric shock;

punished exploration (electric shock for each movement between two ajdacent plates) for 60 seconds.

The electric shocks have a duration of 0.5 secondsand an intensity of 0.6 milliampere.

In each test, the mice are treated by the oral route 60 minutes before the test, either with the pharmacological substances (compounds according to the invention no. 1 505, 1 260, 1 299, 1 503, 1 504, 1 500, 1 406, 1 403, 1 408, 1 502, 1 243, 1 290, 1 294, 1 307, 1 405, 1 213, 1 253, 1 488) or the solvent alone (control batch).

The products are administered in a single dose of 25 mg/kg, orally, by gastric intubation in a 3% carboxymethylcellulose solution, 60 minutes before the test.

The controls receive only carboxymethylcellulose.

EXPRESSION OF THE RESULTS

The results are expressed as percentage of increase in the number of punished passages with respect to the control batch (increase percentage).

RESULTS

They are collected in following table III.

TABLE III

| Four test plates mice ♂ | % increase |
|---|---|
| 1505 | 35 |
| 1260 | 31 |
| 1299 | 28 |
| 1503 | 28 |
| 1504 | 26 |
| 1500 | 25 |
| 1406 | 24 |
| 1403 | 22 |
| 1408 | 22 |
| 1502 | 20 |
| 1243 | 18 |
| 1290 | 17 |
| 1294 | 17 |
| 1307 | 16 |
| 1405 | 14 |
| 1213 | 13 |
| 1263 | 10 |
| 1488 | 10 |

The results of these tests show the anxiolytic activity of the tested compounds. The compounds of the invention no. 1 505, 1 260, 1 299, 1 503, 1 504, 1 500 1 406, 1 403 and 1 408 which have a percentage increase higher than 20% are revealed to be particularly active.

The test with 4 plates has also been carried out on another class of cmpounds according to the invention, using the procedure indicated above and modified as follows.

The mice are treated orally 60 minutes before the test, either with the pharmacological substances (compounds according to the invention no. 1 407, 1 306, 1 426, 1 334, 1 425, 1 428, 1 301, 1 270, 1 265, 1 242, 1 224, 1 247, 1 304, 1 295, 1 211, 1 390, 1 396, 1 274, 1 389, 1 245, 1 427, 1 404, 1 302, 1 214, 1 264, 1 220, 1 400, 1 402 or trimetozine) or the solvent alone (control batch).

The products are administered in a single dose of 5 mg/kg, orally, by gastric intubation, in a 0.1% carboxymethylcellulose solution, 60 minutes before the test.

The controlled receive only carobymethylcellulose.

EXPRESSION OF THE RESULTS

The results are expressed by the index in the variation of the number of punished passages with respect to trimetozine used as a reference (index 100). The index O corresponds to a control batch.

RESULTS

The results obtained are collected in table IV below.

TABLE IV

| Four test plates mice ♂ | Index of variation |
|---|---|
| 1407 | 179 |
| 1306 | 155 |
| 1426 | 154 |
| 1334 | 144 |
| 1425 | 133 |
| 1428 | 133 |
| 1301 | 120 |
| 1270 | 117 |
| 1265 | 107 |
| Trimetozine | 100 |
| 1242 | 97 |
| 1224 | 90 |
| 1247 | 90 |
| 1304 | 85 |
| 1295 | 70 |
| 1211 | 68 |
| 1390 | 64 |
| 1396 | 59 |
| 1274 | 53 |
| 1389 | 52 |
| 1245 | 48 |
| 1427 | 46 |
| 1404 | 43 |
| 1302 | 30 |
| 1214 | 29 |
| 1264 | 22 |
| 1220 | 20 |
| 1400 | 16 |
| 1402 | 16 |

The results of these tests confirm the anxiolytic activity of the compounds of this series.

A preferred class of compounds is constituted by those which have a variation index higher than 50, that is to say the compounds no. 1 407, 1 306, 1 426, 1 334 1 425, 1 428, 1 301, 1 270, 1 265, 1 242, 1 224, 1 247, 1 304, 1 295, 1 211, 1 390, 1 396, 1 274, 1 389.

We claim:

1. A compound corresponding to the formula:

$$SO_2-N \underset{(CH_2)_n}{\diagdown} Z \qquad (I)$$

(attached to a benzene ring with substituents V, W, X, Y)

in which:

V represents hydrogen or an $OR_1$ group in which $R_1$ represents an alkyl group of 1 to 4 carbon atoms;

W represents hydrogen or the $CF_3$ group;

X represents hydrogen, halogen, the $NO_2$, $NH_2$ groups, a $NH-CO-R_2$ group in which $R_2$ represents an alkyl group of 1 to 4 carbon atoms or aryl or an $OR_1$ group in which $R_1$ represents an alkyl group of 1 to 4 carbon atoms;

Y represents hydrogen, halogen, the $NO_2$, $NH_2$, $CF_3$ groups, a $NH-CO-R_2$ group in which $R_2$ represents an alkyl group of 1 to 4 carbon atoms or aryl, an $OR_1$ group in which $R_1$ represents an alkyl group of 1 to 4 carbon atoms or an $SO_2-R_3$ group in which $R_3$ represents an alkyl group of 1 to 4 carbon atoms;

n is 2 or 3; and

Z represents an $NR_4$ group in which $R_4$ represents:
a hydrogen,
a lower alkyl group of 1 to 6 carbon atoms,
a hydroxyalkyl group of 1 to 3 carbon atoms,
a cycloalkanoyl group of 3 to 10 carbon atoms,
an aryl group unsubstituted or substituted by halogen, by the $CF_3$ group, or by an $OR_1$ group in which $R_1$ represents an alkyl group having from 1 to 4 carbon atoms, an aralkyl group in which the aliphatic chain has 1 to 4 carbon atoms and can include C=O and C—OH groups, and in which the aryl group is unsubstituted or substituted by halogen, by the CF₃ group, by an OR₁ group in which R₁ is an alkyl group having from 1 to 4 carbon atoms, or an aroyl group or its isoesters unsubstituted or substituted by halogen, a CF₃ group, or an OR₁ group in which R₁ is an alkyl group of 1 to 4 carbon atoms; provided that, when n=2,

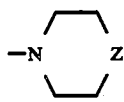

represents a

group and either V represents OR₁, and at least one of the elements W, X or Y is other than hydrogen,
or Y or W represents CF₃.

2. A compound according to claim 1, corresponding to the following formula (IV):

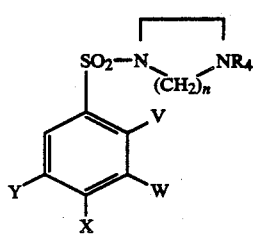
(IV)

in which V, W, X, Y have the meanings indicated in claim 1 and R₄ represents a cyclopropanoyl, cyclopentanoyl, cyclohexanoyl, adamantoyl, benzoyl or furoyl radical.

3. A compound according to claim 1, corresponding to the following formula (IV):

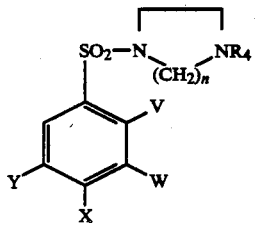
(IV)

in which V, W, X and Y have the meanings indicated in claim 1 and R₄ represents:
- a hydrogen,
- a benzyl group unsubstituted or substituted by halogen, by a CF₃ group, or by an OR₁ group in which R₁ is an alkyl group of 1 to 4 carbon atoms,

—CH₃, CH₂CH₂OH, CH₂CHOHCH₂OH, CH₂—C₆H₅,

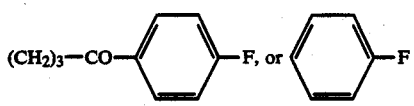

4. A compound according to claim 1, corresponding to the following formula (X):

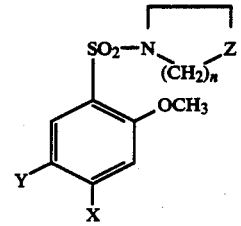
(X)

in which:
n represents 2 or 3;
X represents H, NO₂, or OCH₃;
Y represents H, Cl, Br, OCH₃, SO₂iC₃H₇, or CF₃; and
Z has the meaning indicated in claim 1.

5. A compound according to claim 1, corresponding to the following formula (XI):

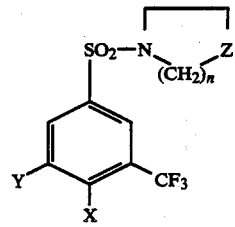
(XI)

in which:
n is 2 or 3;
W represents H or Cl;
Y represents H or CF₃; and
Z has the meaning indicated in claim 1.

6. A compound according to claim 1, corresponding to any one of the following formulae:

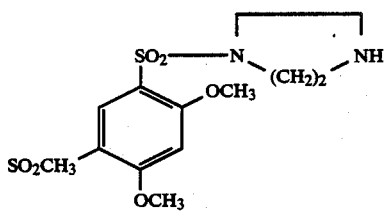

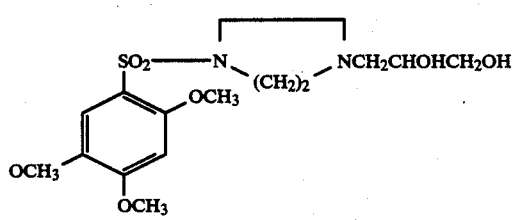

-continued
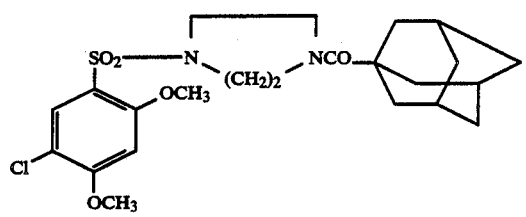
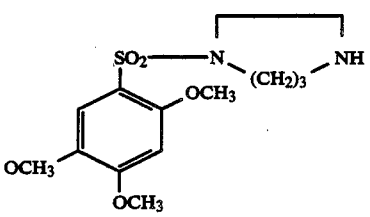
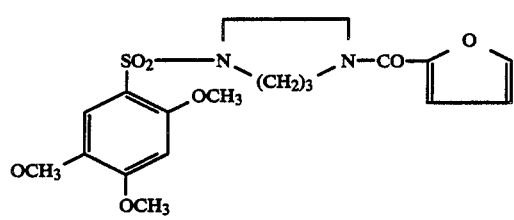
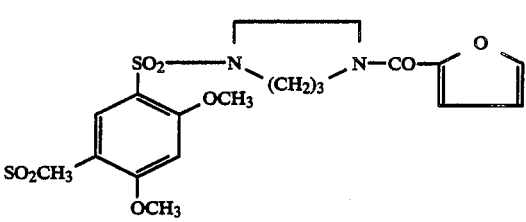
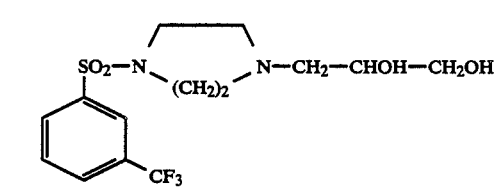
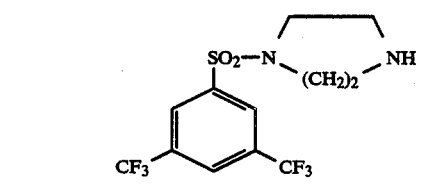
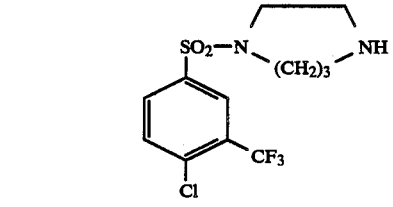
-continued
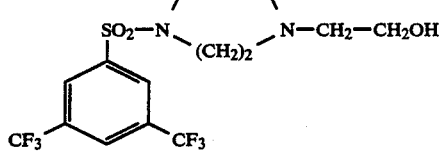
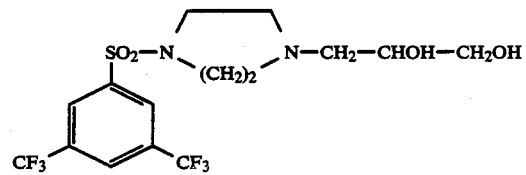
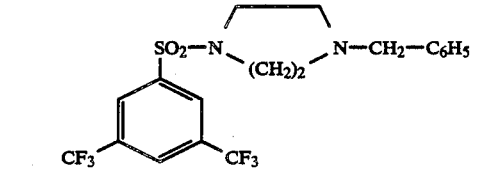
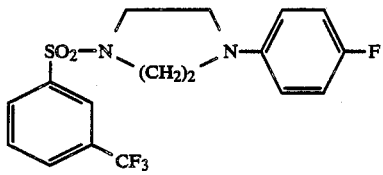
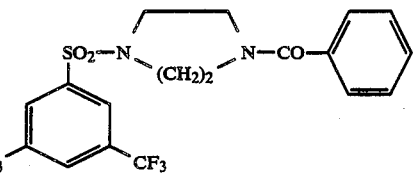
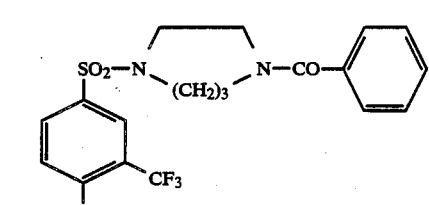
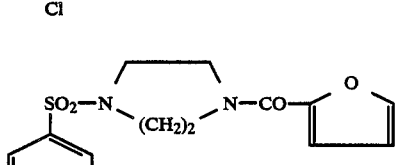
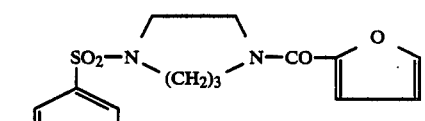

-continued
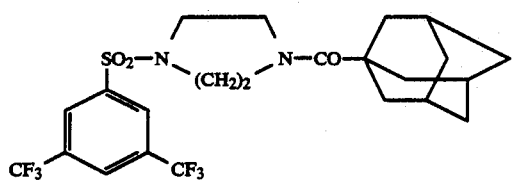
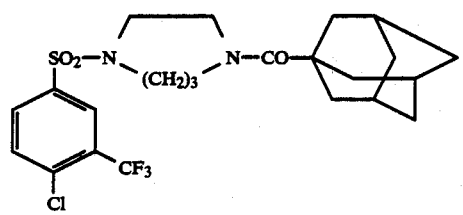
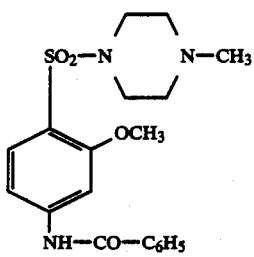
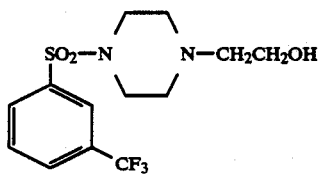
-continued
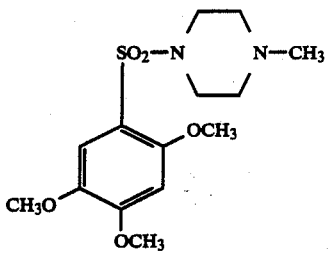
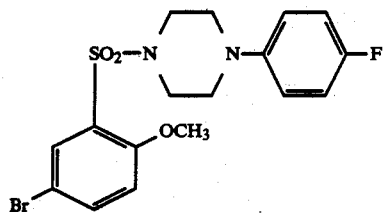
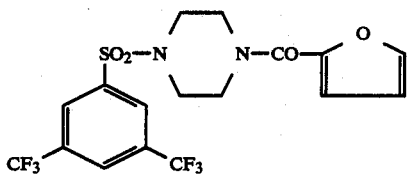
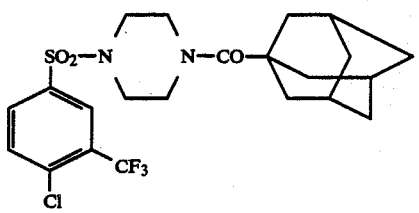
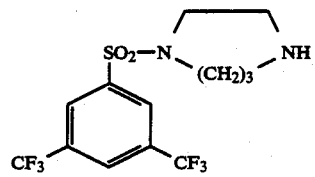
* * * * *